(12) United States Patent
Chuang

(10) Patent No.: US 8,173,033 B2
(45) Date of Patent: May 8, 2012

(54) MANUFACTURING METHOD OF A NANO FILTER STRUCTURE FOR BREATHING

(76) Inventor: Shu-Yuan Chuang, Miaoli County (TW)

( * ) Notice: Subject to any disclaimer, the term of this patent is extended or adjusted under 35 U.S.C. 154(b) by 0 days.

(21) Appl. No.: 13/316,244

(22) Filed: Dec. 9, 2011

(65) Prior Publication Data

US 2012/0080405 A1   Apr. 5, 2012

Related U.S. Application Data

(62) Division of application No. 12/578,119, filed on Oct. 13, 2009, now Pat. No. 8,101,129.

(51) Int. Cl.
*B23P 15/00* (2006.01)
*C03C 25/00* (2006.01)
*C23F 1/00* (2006.01)
*B01D 50/00* (2006.01)

(52) U.S. Cl. ............... 216/39; 216/17; 216/18; 216/56; 977/700; 977/762; 977/767

(58) Field of Classification Search .................. 55/483; 128/205.29
See application file for complete search history.

(56) References Cited

U.S. PATENT DOCUMENTS

| 5,948,255 A | 9/1999 | Keller |
| 2005/0184003 A1* | 8/2005 | Rodgers et al. .......... 210/321.75 |
| 2011/0129757 A1 | 6/2011 | Diem |

* cited by examiner

*Primary Examiner* — Shamim Ahmed
*Assistant Examiner* — Bradford Gates
(74) *Attorney, Agent, or Firm* — Muncy, Geissler, Olds & Lowe, PLLC

(57) ABSTRACT

In a nano filter structure for breathing and a manufacturing method of the nano filter structure, a semiconductor process technology is used for manufacturing a nano filter structure comprising a top gate, a bottom gate, a plurality of sidewall gates and a plurality of supports. The sidewall gates include a plurality of filterable gratings, and the filterable gratings are controlled precisely to a nanoscale by a semiconductor process technology. Therefore, the nano filterable gratings can be manufactured easily and quickly, and the multilayer design of the filterable gratings enhances the aperture ratio of a filter material, such that users can inhale or exhale easily through the filter material.

7 Claims, 24 Drawing Sheets

MANUFACTURING METHOD OF A NANO FILTER STRUCTURE FOR BREATHING

CROSS-REFERENCE TO RELATED APPLICATIONS

This application is a Divisional of application Ser. No. 12/578,119, filed on Oct. 13, 2009, now U.S. Pat. No. 8,101,129, for which priority is claimed under 35 U.S.C. §120, the entire contents of which are hereby incorporated by reference.

FIELD OF THE INVENTION

The present invention relates to a filter structure and a manufacturing method of the filter structure, and more particularly to a nano filter structure for filtering air during breathing and a manufacturing method of the nano filter structure.

BACKGROUND OF THE INVENTION

As commerce and industry advance, the number of densely populated cities increases, and the air pollution caused by human activities becomes increasingly worse. In recent years, the air pollution due to the exhaust gas discharge of automobiles and motor cycles, massive petroleum consumption, and dispersion of various different harmful air pollutants jeopardizes the health of people who have been living in the air polluted environment for a long time, and thus people pay more attentions to the air quality of the environment.

On the other hand, viruses, bacteria and toxic dusts directly affecting our health are always our major concerns, and people attempt using a filter material to isolate viruses and bacteria, so that the viruses and bacteria cannot enter our breathing system or cause infections. At present, most filters are filter nets made of stacked fibers, such as a multi-layer filter net with a substrate made of polypropylene (PP), and filter layers of this type are applied to the manufacture of masks, face masks, nose filters or breathing apparatus.

Masks are generally divided according to their applications into dust masks, activated carbon masks and medical N95 masks certified by National Institute for Occupational Safety and Health (NIOSH). The N95 mask comes with a dense fiber structure capable of isolating 95% of tiny particles having a size over 0.3 µm), and thus the N95 mask provides a better protective effect than the dust mask and activated carbon mask.

In general, bacteria having a diameter of over 0.3 µm can be isolated by the N95 mask easily as shown in Table 1, but viruses with a nanoscale diameter (which is much smaller than the bacteria with a micro diameter) cannot be isolated by the N95 mask. For example, the virus of severe acute respiratory syndrome (SARS) has a diameter of 100~120nm only and the N95 mask is unable to effectively isolate or prevent the SARS virus from passing through the mask.

TABLE 1

| | Type | Diameter (µm) | Related Disease |
|---|---|---|---|
| Virus | Orthomyxoviridae | 0.08~0.12 | Influenza Types A, B and C |
| | Coronaviridae | 0.10~0.12 | SARS |
| Bacteria | Serratia Marcescens | 1.0~5.0 | Nosocomial Infections |
| | Mycobacterium Tuberculosis | 0.45 | Tuberculosis |

Therefore, a conventional filter structure manufactured by a fiber stacking technology just has a protective effect up to a micron scale, but almost has no effect for viruses in a nanoscale.

Relatively, the filter can limit the size of transmitting particles, and thus a refined filter structure may give rise to an uncomfortable breathing pressure to users. In other words, the smaller the aperture ratio of the filter material, the lower is the level of ventilation. As a result, users have difficulties inhaling or exhaling normally through the filter material.

SUMMARY OF THE INVENTION

Therefore, it is an objective of the present invention to overcome the aforementioned shortcomings of the prior art by providing a nano filter structure for breathing and a manufacturing method of the nano filter structure to filter viruses, bacteria, toxic dusts . . . etc. effectively.

Another objective of the present invention is to provide a nano filter structure for breathing and a manufacturing method of the nano filter structure to facilitate improving an aperture ratio.

A further objective of the present invention is to provide a nano filter structure for breathing and a manufacturing method of the nano filter structure to improve the life time of the filter structure.

To achieve the foregoing and other objectives, the present invention provides a nano filter structure for breathing, and the nano filter structure comprises: a top gate, having a plurality of top openings; a bottom gate, disposed parallel to the top gate, and having a plurality of bottom openings, and the bottom openings and the top openings being disposed alternately with each other; a plurality of sidewall gates, disposed between the top gate and the bottom gate and adjacent to a top opening and a bottom opening, and each sidewall gate having a plurality of filterable gratings parallel to the top gate and the bottom gate to form a plurality of filter channels; and a plurality of supports, disposed between the top gate and the bottom gate and at an intersection of two sidewall gates, wherein the filter channels have a channel height below 300 nm.

To achieve the foregoing and other objectives, the present invention provides a nano filter structure for breathing and a manufacturing method of the nano filter structure in accordance with a preferred embodiment, and the nano filter structure comprises a plurality of top opening regions, a plurality of bottom opening regions, a plurality of sidewall gate regions and a plurality of support regions, and each sidewall gate region is disposed adjacent to a top opening region and a bottom opening region, and each support region is disposed at an intersection of two sidewall gate regions. The manufacturing method comprises the steps of: (A1) forming a patterned lifter layer on a substrate; (A2) forming a patterned first support layer on a portion of the lifter layer and a portion of the substrate, such that the bottom opening regions do not include the first support layer; (A3) forming a patterned first sacrificial layer separately on the lifter layer of the bottom opening region, and the first support layers of the top opening regions and the sidewall gate regions; (A4) forming a patterned second support layer separately on the sidewall gate regions and the support regions; (A5) forming a patterned second sacrificial layer separately on the top opening regions, the bottom opening regions and the sidewall gate regions; (A6) forming a top gate layer separately on the top sacrificial layers of the bottom opening regions and the sidewall gate regions, and the top support layer of the support regions; (A7) removing all sacrificial layers and the lifter layer; and (A8)

removing the substrate; wherein each sacrificial layer so formed has a thickness smaller than or equal to 300 nm. After Step (A5) takes place, the manufacturing method further comprises a Step (A5-1) that repeats Steps (A4) and (A5) in sequency to form a plurality of support layers and a plurality of sacrificial layers.

To achieve the foregoing and other objectives, the present invention provides a manufacturing method of a nano filter structure for breathing in accordance with a second preferred embodiment, and the nano filter structure comprises a plurality of top opening regions, a plurality of bottom opening regions, a plurality of sidewall gate regions and a plurality of support regions, and each sidewall gate region is adjacent to a top opening region and a bottom opening region, and the support regions are disposed at an intersection of two sidewall gate regions, and the manufacturing method comprises the steps of: (B1) forming a patterned lifter layer on a substrate; (B2) forming a patterned first support layer on a portion of the lifter layer and a portion of the substrate, such that the bottom opening regions do not include the first support layer; (B3) forming a patterned first sacrificial layer separately on the bottom opening regions, the top opening regions and the sidewall gate regions; (B4) forming a patterned second support layer separately on the sidewall gate regions and the support regions; (B5) forming a second sacrificial layer separately on the top opening regions, the bottom opening regions, the sidewall gate regions and the support regions; (B6) forming a third support layer separately on the top opening regions, the bottom opening regions, the sidewall gate regions and the support regions; (B7) forming a protective layer separately on the top opening regions, the bottom opening regions, the sidewall gate regions and the support regions; (B8) etching the support regions and removing at least the third support layer to form a support groove in each support region; (B9) laterally etching the support grooves and removing a portion of the sacrificial layers to form a plurality of support side-wing grooves; (B10) filling the support grooves and the support side-wing grooves to form a plurality of fillers; (B11) etching the top opening regions and the bottom opening regions and removing at least the third support layer; (B12) forming a patterned first channel sacrificial layer separately on the top opening regions, the bottom opening regions, the sidewall gate regions and a portion of the support regions; (B13) forming a top gate layer separately in the bottom opening regions, the sidewall gate regions and the support regions; (B14) removing the lifter layer and all sacrificial layers; and (B15) removing the substrate; wherein each sacrificial layer so formed has a thickness smaller than or equal to 300 nm.

In the second preferred embodiment, after Step (B6) takes place, the manufacturing method further comprises a step (B6-1) that repeats Steps (B5) and (B6) in sequency to form a plurality of support layers and a plurality of sacrificial layers. And the finally formed layer in Step (B6-1) is a sacrificial layer.

In the second preferred embodiment, after Step (B12) takes place, the manufacturing method further comprises a step (B12-1) that forms a patterned first channel support layer separately on the sidewall gate regions and the support regions; and a step (B12-2) that repeats Steps (B12) and (B12-1) in sequency to form a plurality of channel support layers and a plurality of channel sacrificial layers, and the finally formed layer is a channel sacrificial layer.

In the preferred embodiments of the present invention, the length of the sides of the top openings and the bottom openings are in a length of a micro scale. The periphery of the top openings and the bottom openings has the sidewall gates. Each support includes a filler made of a polymer material. The top of the top gate further includes a thin film for decomposing organic matters.

The present invention uses a semiconductor process technology to manufacture the nano filter structure to achieve manufacturing a filterable grating in a nanoscale, and make the manufacture of the nano filter structure more quickly. Airflow can be convected into either the top gate or the bottom gate of a micron scale for a preliminary filtering of a micron scale, so as to extend the life of the filter material. In addition, the design of the multi-layer filterable grating can increase the aperture ratio of the filter material, such that users can inhale or exhale through the filter material easily.

DESCRIPTION OF THE PREFERRED EMBODIMENT

Other features and advantages of the present invention will become apparent in the following detailed description of the preferred embodiments with reference to the accompanying drawings.

As semiconductor process technology and panel manufacturing process technology become well-developed, these technologies provide a precise control of the thickness of thin films and produce a thin film with a thickness in a nano scale easily. The present invention uses a non-toxic material and a thin film deposition process such as sputtering, physical vapor deposition or chemical vapor deposition commonly used in the semiconductor process technology or panel manufacturing process technology to produce thin films with a thickness of nanometers, and then uses an etching technology such as dry etching, wet etching or gas etching used in the semiconductor process technology or panel manufacturing process technology for a selective etch with different etch ratios. Therefore, materials with different etch ratios and an appropriate etch mode can be used for etching adjacent materials having different stacked structures to form a grating channel structure. The semiconductor process technology or panel manufacturing process technology adopted by the invention not just controls the thickness of the stacked layer structure precisely, but also manufactures the nano filter structure quickly. An increased number of stacked layers can increase the volume of intake and output air of the airflow to improve the aperture ratio of filter structure.

Figure 1:
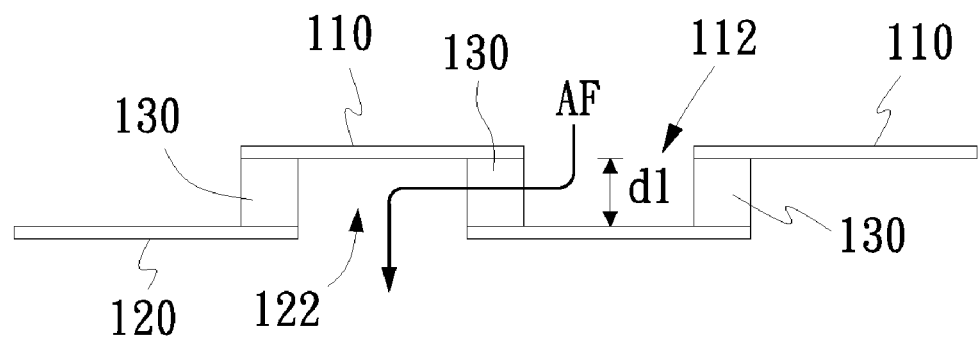
FIG. 1 is a cross-sectional view of a nano filter channel in accordance with a preferred embodiment of the present invention.

With reference to FIG. 1 for a cross-sectional view of a nano filter channel in accordance with a preferred embodiment of the present invention, the nano filter structure comprises a top gate 110, a bottom gate 120 and a plurality of supports 130, wherein an airflow AF enters from a top opening 112 of the top gate 110, passes through a filter channel formed by the support 130 of a distance d1, and then flows out from a bottom opening 122 of the bottom gate 120. With a control of the thickness of the support 130, the invention can determine a filter grade of the filter channel, and the nano filter structures can be manufactured with a high aperture ratio.

Figure 2:
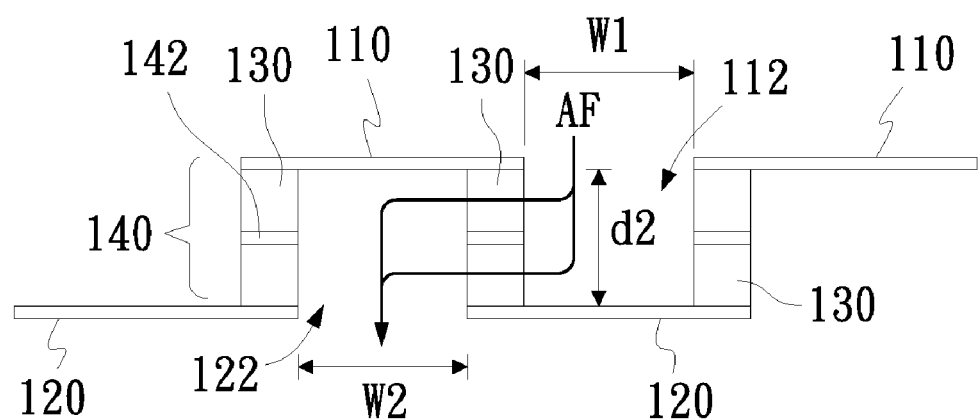
FIG. 2 is a cross-sectional view of a nano filter channel in accordance with another preferred embodiment of the present invention.

With reference to FIG. 2 for a cross-sectional view of a nano filter channel in accordance with another preferred embodiment of the present invention, the number of stacked layers of the supports 130 can be increased in a manufacturing process to improve the aperture ratio of a filter material, and the quantity of stacked layers or the thickness of the supports 130 can be increased to increase the distance d2 between the top gate 110 and the bottom gate 120, and a multi-layer sidewall gate 140 comprised of a plurality of filterable gratings 142 is formed at the filter channel. In a preferred embodiment as shown in FIG. 2, there are two filter channels, and the distance between the filterable grating 142 and the top gate 110 or the bottom gate 120 is d1 (as shown in FIG. 1). The distance d2 between the top gate 110 and the bottom gate 120 increases with an increased number of stacked layers or an increased thickness of the supports 130, such that more filter channels can be formed in the sidewall gate 140. Both of the aforementioned distances d1, d2 controlled by the manufacturing process (including sputtering, physical vapor deposition, chemical vapor deposition or other equivalent manufacturing process) can be used for determining the height. Compared with FIG. 1, FIG. 2 shows one more filter channel, so that the airflow AF can flow in a multiple of paths to increase the aperture ratio of the filter channel effectively. In addition, a distance w2 between the top opening 112 of the top gate 110 and the bottom opening 122 of the bottom gate 120 can be controlled by a mask design and a yellow light manufacturing process to form micron openings for performing a preliminary filter (for nanoparticles that enter into the airflow AF.)

Figure 3:
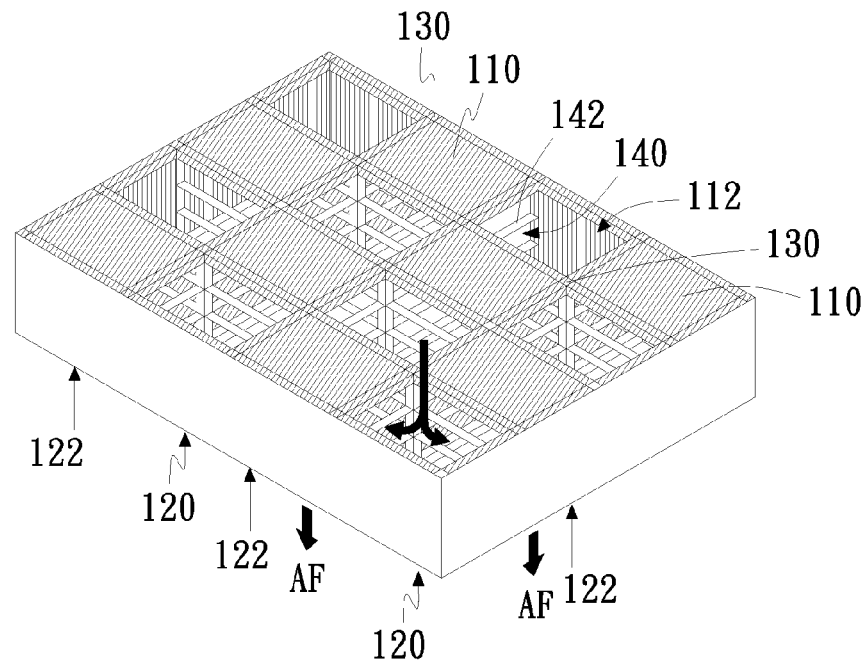
FIG. 3 is a perspective view of a nano filter channel in accordance with a preferred embodiment of the present invention.

With reference to FIG. 3 for a perspective view of a nano filter structure in accordance with a preferred embodiment of the present invention, a semiconductor process technology or panel manufacturing process technology of this preferred embodiment is used to quantify the structure of the forgoing preferred embodiment as illustrated in FIG. 2. In FIG. 3, the top gate 110 includes eight top openings 112, wherein an opposite side (which is the bottom side) of the top gate 110 includes eight bottom openings 122, and the opposite side (or the bottom side) of the top opening 112 is the bottom gate 120. FIG. 3 simply shows an embodiment, but the area of the filter structure and the quantity of openings depend on actual requirements of the practical application.

Figure 4:
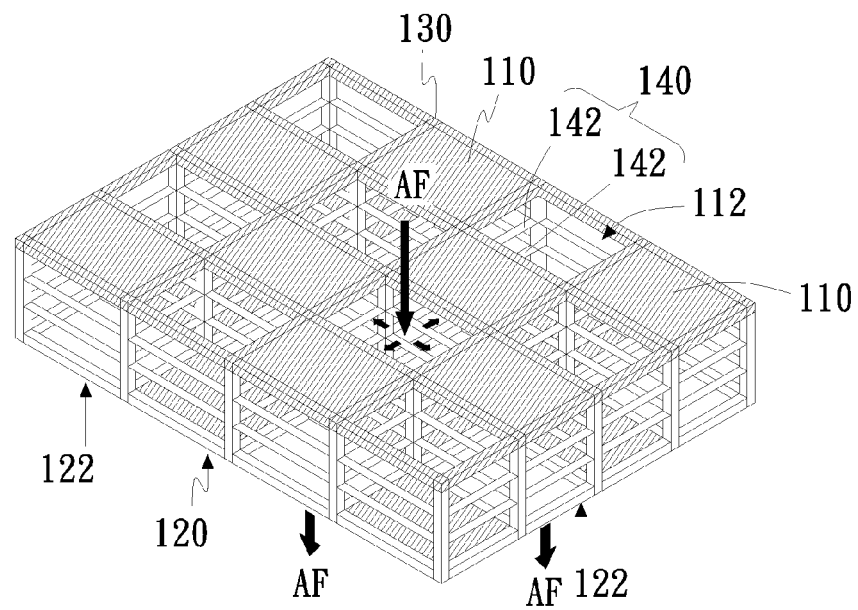
FIG. 4 is a perspective view of a nano filter channel in accordance with another preferred embodiment of the present invention.

With reference to FIG. 4 for a perspective view of a nano filter structure in accordance with another preferred embodiment of the present invention, the nano filter structure includes the sidewall gate 140 disposed around the nano filter structure. In the preferred embodiment as shown in FIGS. 3 and 4, the semiconductor process technology or panel manufacturing process technology can be used for manufacture the nano filter structure.

Figure 5:
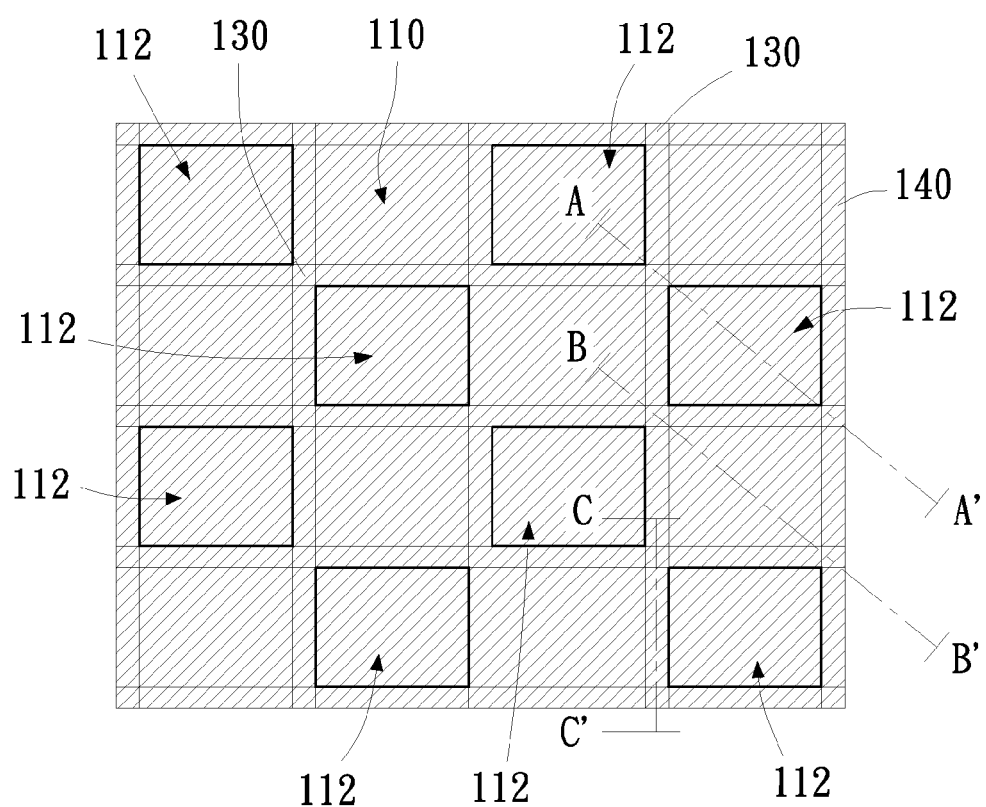
FIG. 5 is a top view of a nano filter channel as depicted in FIGS. 3 and 4.

With reference to FIG. 5 for a top view of a nano filter structure, a cross-section AA' of the bottom gate, a cross-section BB' of the top gate, and a cross-section CC' of the sidewall gate are used for illustrating the manufacturing flow of the top opening region, the bottom opening region, the sidewall gate region and the support region in the manufacturing procedure. The shapes of the top openings 112, the top gates 110, the supports 130 and the sidewall gates 140 are provided here for the illustration purpose only, but any equivalent shape can be used for the filter structure of the present invention without departing the spirit and scope of the invention. For clarity and comparison of the cross-sections of the top opening region, the bottom opening region, the sidewall gate region and the support region in each step of the manufacturing procedure, the cross-section CC' of sidewall gate as shown in FIG. 5 is enlarged to a size equal to the cross-section AA' of the bottom gate and the cross-section BB' of the top gate.

With reference to FIGS. 6 to 11 for cross-sectional views of a manufacturing process of a nano filter structure in accordance with a first preferred embodiment, FIGS. 6A to 11A show cross-sectional views of a bottom gate along a cross-section line AA' during the manufacturing process as depicted in FIG. 5, FIGS. 6B to 11B show cross-sectional views of a top gate along a cross-section line BB' during the manufacturing process as depicted in FIG. 5, FIGS. 6C to 11C show cross-sectional views of a sidewall gate along a cross-section line CC' during the manufacturing process as depicted in FIG. 5. The present invention adopts a semiconductor process technology or panel manufacturing process technology to manufacture a nano filter structure, and each layer of the nano filter structure is formed in the manufacturing process of the invention by sputtering, chemical vapor deposition (CVD), physical vapor deposition (PVD) or any other equivalent method, and the patternization conducted by the semiconductor process technology or panel manufacturing process technology refers to a lithography and an etching technology, wherein the etching technology includes dry etching, wet etching, gas etching or any other equivalent etch mode.

Figure 6A:
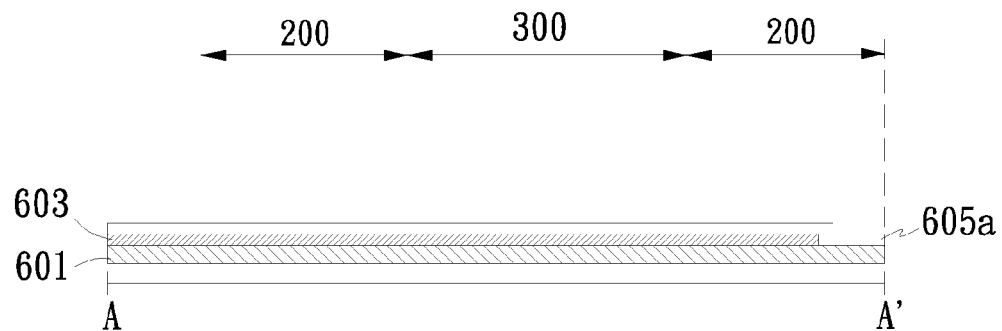
FIGS. 6 A-C, 7 A-C, 8 A-C, 9 A-C, 10 A-C, and 11 A-C are cross-sectional views of a manufacturing flow of a nano filter structure in accordance with a first preferred embodiment of the present invention.
Figure 6B:
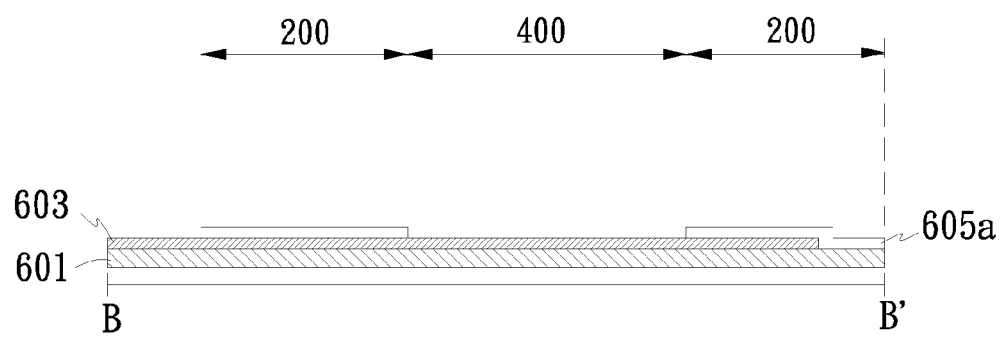
Figure 6C:
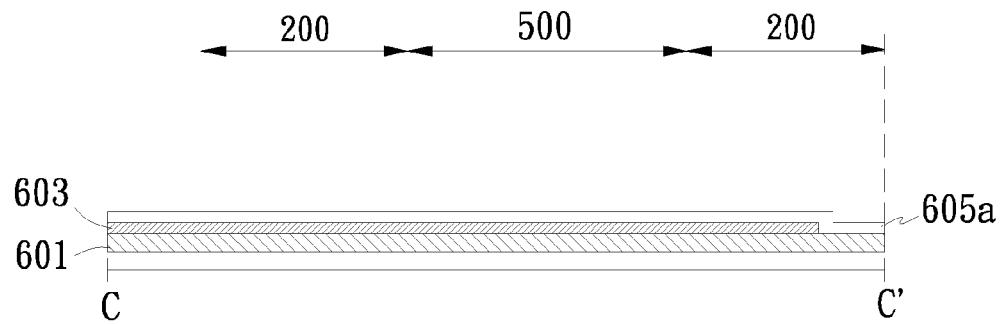

In the first preferred embodiment as shown in FIGS. 6A, 6B and 6C, the nano filter structure comprises a support region 200, a top opening region 300, a bottom opening region 400 and a sidewall gate region 500. In Step (A1), a substrate 601 such as a glass substrate, a wafer substrate, a plastic substrate or any other equivalent substrate is provided, and then a patterned lifter layer 603 is formed on the substrate 601. In Step (A2), a patterned first support layer 605a is formed on a portion of the lifter layer 603 and a portion of the substrate 601. In other words, the lifter layer 603 of the support region 200, the top opening region 300 and the sidewall gate region 500 has the first support layer 605a, and the bottom opening region 400 does not include the first support layer 605a.

Figure 7A:
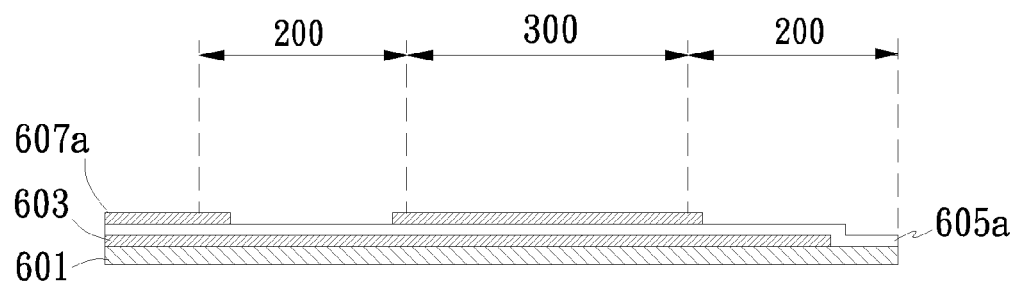
Figure 7B:
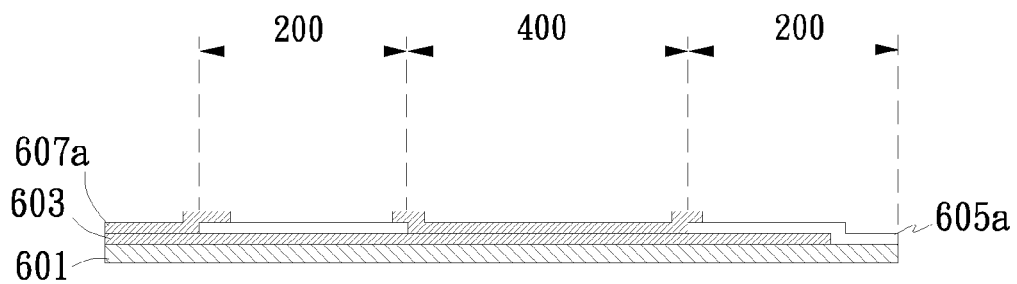
Figure 7C:
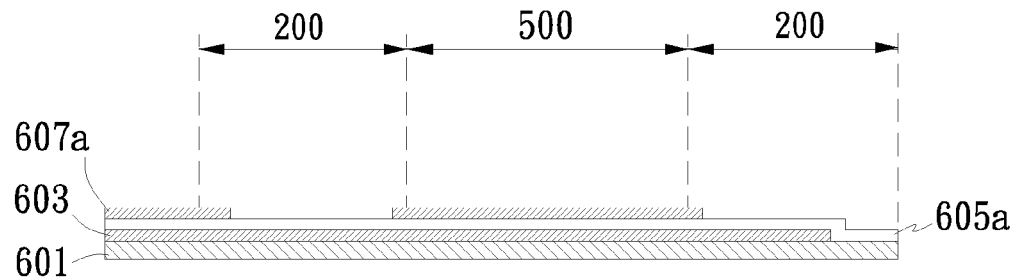

With reference to FIGS. 7A, 7B and 7C for Step (A3), sputtering, chemical vapor deposition, physical vapor deposition or any other equivalent method is used and lithography and etching are performed to form a first sacrificial layer 607a on the lifter layer 603 of the bottom opening region 400, and on the first support layer 605a of the top opening region 300 and the sidewall gate region 500, wherein the sacrificial layer will be removed last. The present invention controls the filter grade of the filter channel by the thickness of the sacrificial layer. With the semiconductor process technology or panel manufacturing process technology, the thickness of the film layer can be controlled easily and precisely. The thickness (or height) of the sacrificial layer is controlled to be smaller than or equal to 300 nm, so that the filter channel can provide the effect of filtering viruses.

Figure 8A:
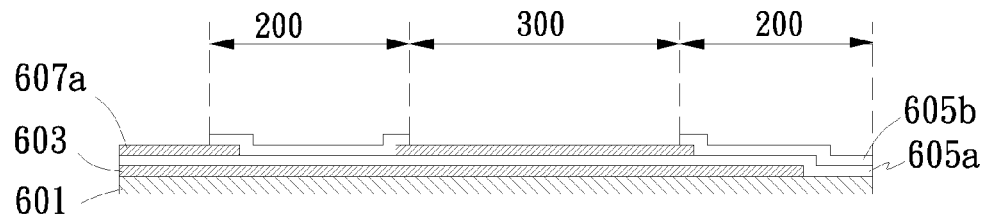
Figure 8B:
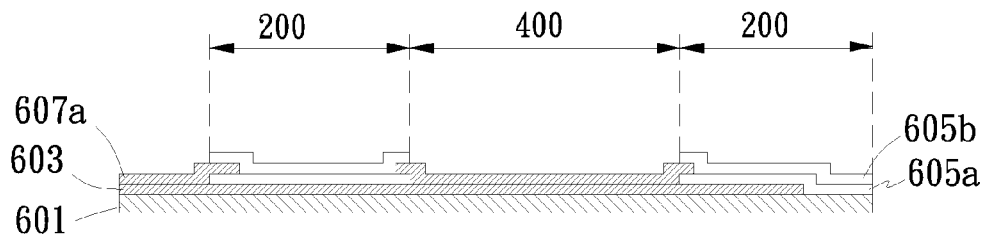
Figure 8C:
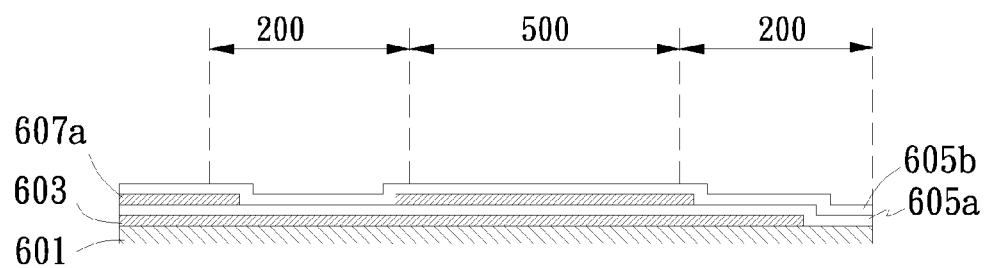

With reference to FIGS. 8A, 8B and 8C for Step (A4), sputtering, chemical vapor deposition, physical vapor deposition or any other equivalent method as well as lithography and etching technology are used to form a second support layer 605b on the first sacrificial layer 607a of the sidewall gate region 500 and the first support layer 605a of the support region 200. In FIG. 8C, the second support layer 605b of the support region 200 and the sidewall gate region 500 are continuous layered structures, and a filterable grating 142 as shown in FIGS. 2 to 4 is formed on the support layer in the sidewall gate region 500. In FIGS. 8A, 8B and 8C, a bottom gate 120 as shown in FIGS. 2 to 4 is formed on the first support layer 605a of the support region 200, the top opening region 300 and the sidewall gate region 500.

Figure 9A:
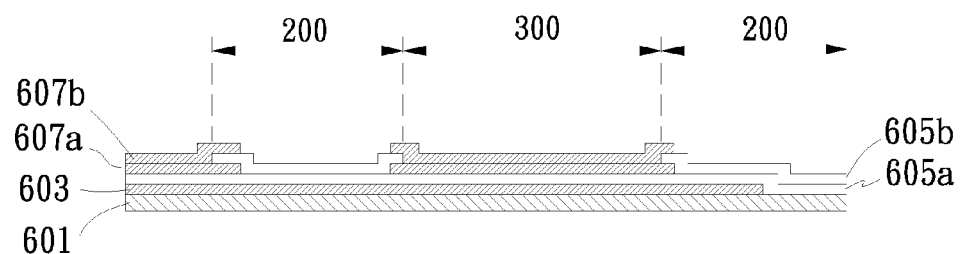
Figure 9B:
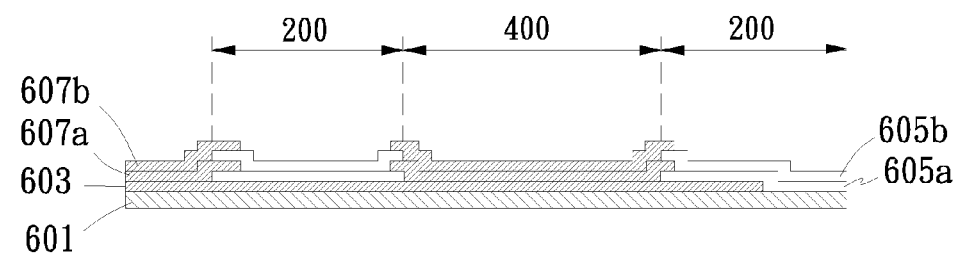
Figure 9C:
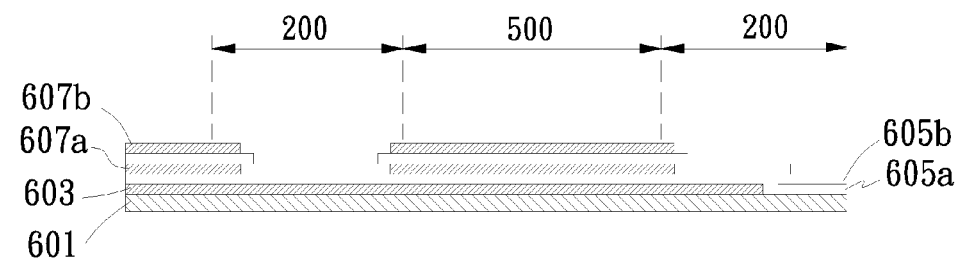

With reference to FIGS. 9A, 9B and 9C for Step (A5), sputtering, chemical vapor deposition, physical vapor deposition or any other equivalent method as well as lithography and etching technology are used to form a second sacrificial layer 607b on the first sacrificial layer 607a of the top opening region 300 and the bottom opening region 400 and the second support layer 605b of the sidewall gate region 500.

Figure 10A:
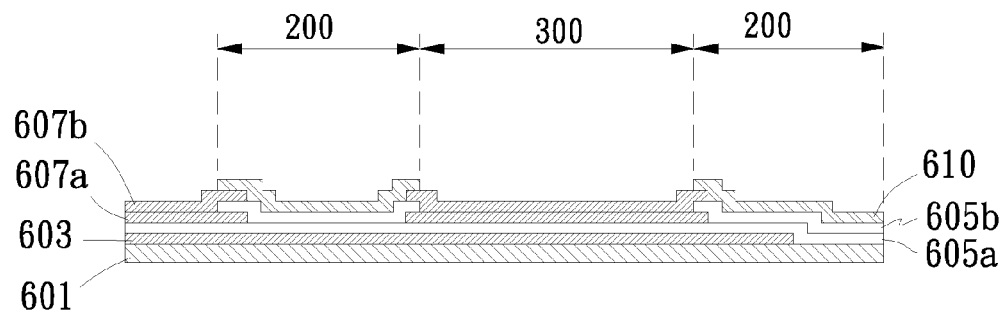
Figure 10B:
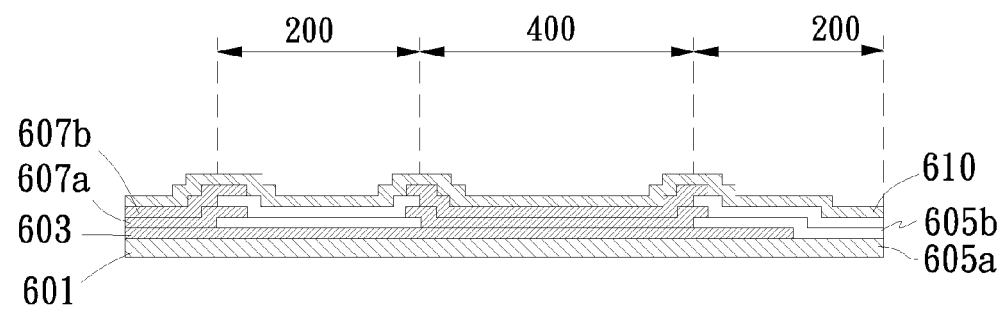
Figure 10C:
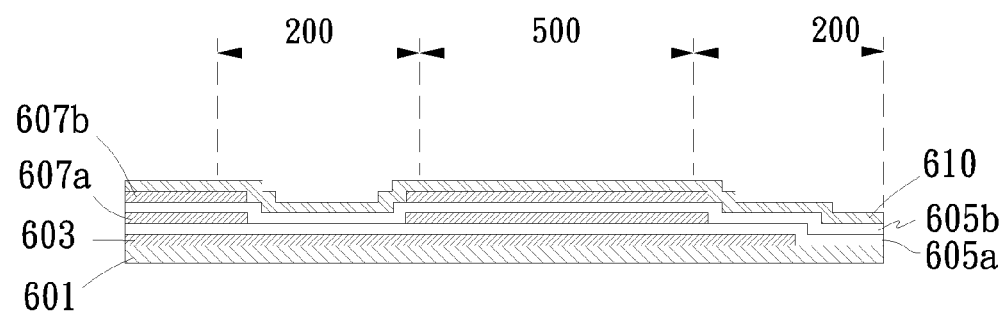

With reference to FIGS. 10A, 10B and 10C for Step (A6), sputtering, chemical vapor deposition, physical vapor deposition or any other equivalent method as well as lithography and etching technology are used to form a top gate layer 610 on the top sacrificial layer (which is the second sacrificial layer 607b) of the bottom opening region 400 and the sidewall gate region 500, and the top support layer (which is the second support layer 605b) of the support region 200. In FIG. 10B, a top gate 110 as shown in FIGS. 2 to 4 is formed on the top gate layer 610 of the bottom opening region 400.

Figure 11A:
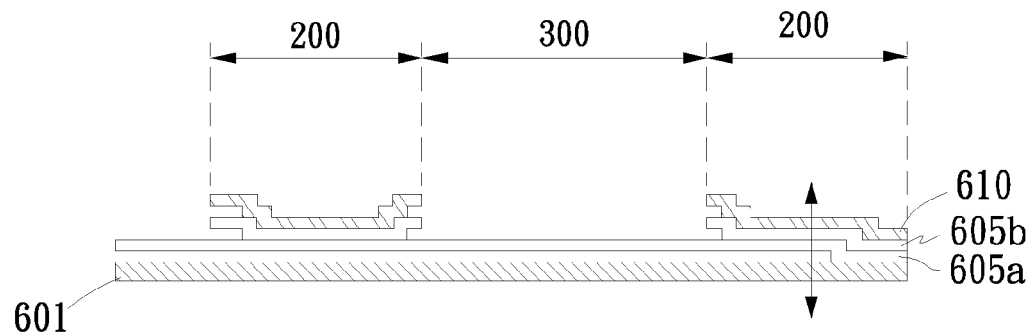
Figure 11B:
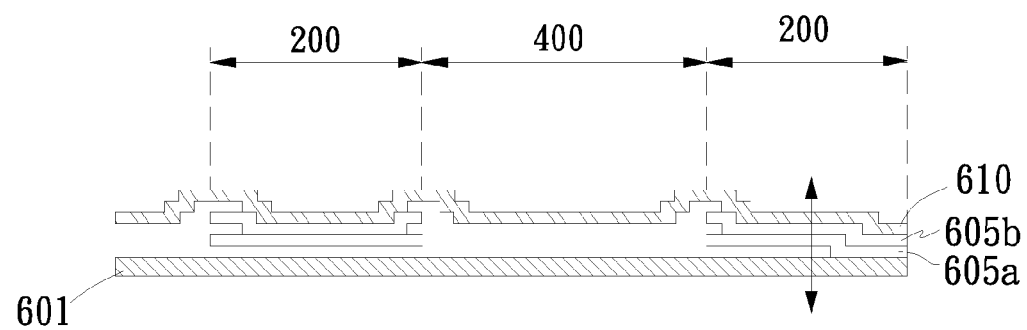
Figure 11C:
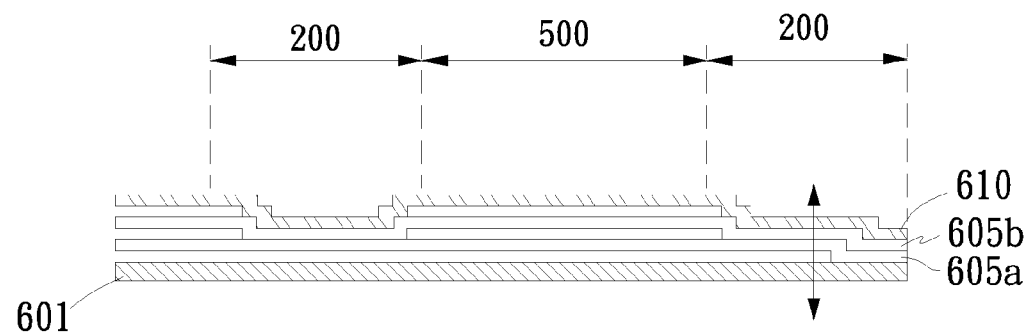

With reference to FIGS. 11A, 11B and 11C for Step (A7), a final etch is performed, and an etching technology such as dry etching, wet etching, gas etching or any other equivalent method is used to remove the lifter layer 603 and all sacrificial layers 607a, 607b. Finally, Step (A8) is carried out to remove the substrate 601 to form a nano filter structure as shown in FIGS. 3 and 4. The method of removing the substrate 601 can be achieved by a scribe or any other equivalent scribe and break technology. Of course, persons ordinarily skilled in the art of the semiconductor process technology or panel manufacturing process technology should understand that different side structures as shown in FIGS. 3 and 4 can be achieved by a photomask design of the manufacturing process. Finally, the nano filter structure can be assembled together with other fixing devices to form a filter can, a filter layer of a respiratory mask or a filter layer in a mask or a nose filter.

Figure 12A:
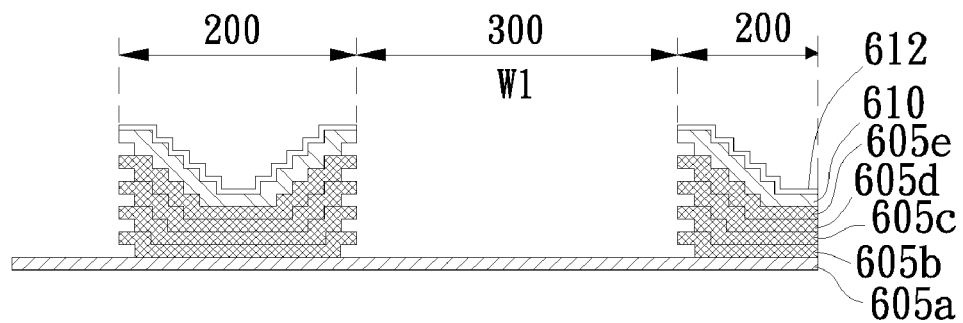
FIGS. 12 A to 12 C are a cross-sectional view of a portion of a nano filter structure having five filter channels.
Figure 12B:
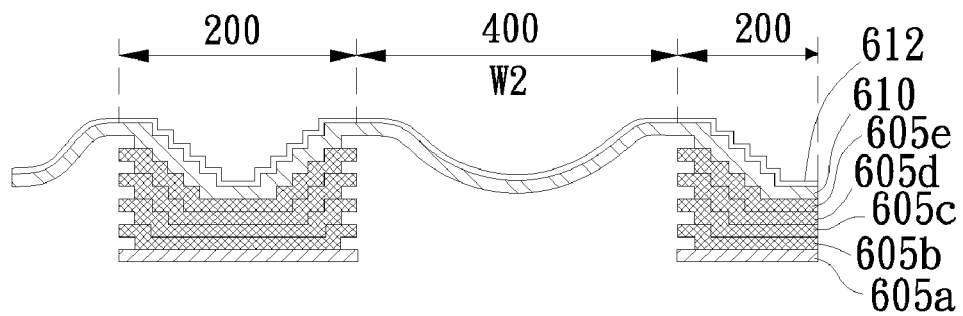
Figure 12C:
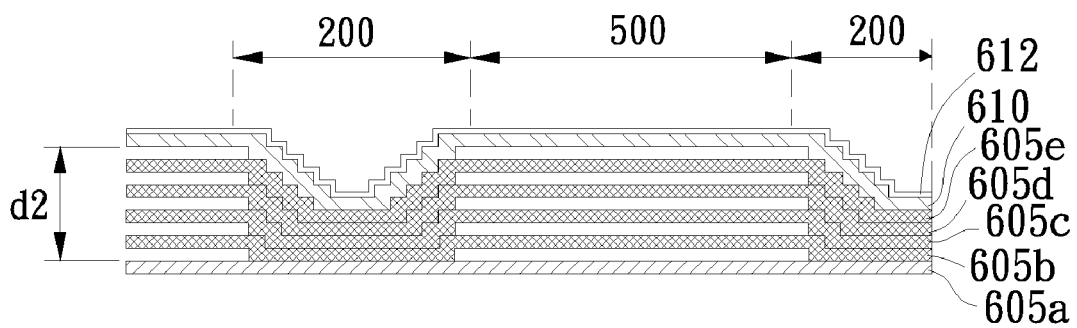

With reference to FIGS. 12A, 12B and 12C for cross-sectional views of a portion of a nano filter structure having five filter channels, w1, w2 and d2 in these figures correspond to the w1, w2 and d2 in FIGS. 1 and 2. The first to fifth support layers correspond to 605a to 605e, and the first to fifth sacrificial layers are removed and not shown in these figures. The manufacturing method of a nano filter structure having two filter channels as shown in FIGS. 6 to 11 has been described above, but more filter channels can increase the aperture ratio. Based on the aforementioned method, a Step (A5-1) can be added after Step (A5) takes place. In Step (A5-1), Steps (A4) and (A5) of the manufacturing process as shown in FIGS. 8 and 9 are carried out in sequency to increase the number of filter channels. In other words, the support layers and the sacrificial layers are stacked alternately to form more filter channels. In the nano filter structure having five channels as shown in FIG. 12, an airflow enters from the top opening region 300, passes through the sidewall gate region 500 for a nano filtering process, and flows out from the bottom opening region 400. On the other hand, the airflow enters into the bottom opening region 400, passes through the sidewall gate region 500, and flows out from the top opening region 300 for exhalation. Persons ordinarily skilled in the art should know that the airflow flows through the sidewall gate region 500 regardless of inhalation or exhalation, and the airflow may also enter from the bottom opening region 400 instead of the top opening region 300 for inhalation. In other words, the nano filter structure is not limited to a single direction for its application, but both upper and lower sides of the nano filter structure can be used as an inhaling side.

In the first preferred embodiment, the manufacturing method further comprises a Step (A6-1) after Step (A6) takes place, or before the lifter layer 603 and all sacrificial layers 607a, 707b are removed. In Step (A6-1), a thin film 612 (as shown in FIGS. 12A, 12B and 12C) is formed on the top gate layer 610 for decomposing an organic matter, wherein the thin film 612 can be made of titanium (Ti), titanium dioxide ($TiO_2$), or platinum (Pt) for resisting or killing viruses and bacteria, and these materials serve as a catalyst for decomposing an organic matter on the filter structure. The thin film 612 can be formed by physical vapor deposition, chemical vapor deposition, sputtering or any other equivalent manufacturing process.

In the first preferred embodiment, the lifter layer 603, the support layers 605a~605e, the sacrificial layers 607a~607e and the top gate layer 610 are made of a material capable of maintaining the support layers 605a~605e and the top gate layer 610 after the lifter layer 603 and the sacrificial layers 607a~607e are etched. Tables 2 to 7 list the materials, the etch modes of etching each film layer, and the final etch (for removing the lifter layer and all sacrificial layers) in accordance with a first preferred embodiment, and persons ordinarily skilled in the art should understand that the materials and etch modes are not limited to the preferred embodiment only, but any equivalent material and etch mode can be used for the nano filter structure of the invention without departing the scope of the present invention, and the composition used for the PAN wet etching includes (Phosphorus acid+Acetic acid+Nitric acid)aq, and the composition of the BOE wet etching includes ($HF+NH_4F$)aq.

TABLE 2

| Choice 1 | | |
|---|---|---|
| Name | Material | Etch Mode |
| Lifter layer (603) | Molybdenum (Mo) | PAN wet etching or dry etching ($Cl_2/SF_6$) |
| Support layer (605) | Silicon oxide (SiOx) | BOE wet etching |
| Sacrificial layer (607) | Molybdenum (Mo) | PAN wet etching or dry etching ($Cl_2/SF_6$) |
| Top gate layer (610) | Silicon oxide (SiOx) | BOE wet etching |
| Thin film (612) | Titanium oxide (TiOx) | dry etching ($Cl_2$) or wet etching (Hydrogen Peroxide) |
| Final etch | Etching Molybdenum (Mo) | PAN wet etching or gas etching ($XeF_2$) |

TABLE 3

Choice 2

| Name | Material | Etch Mode |
|---|---|---|
| Lifter layer (603) | Amorphous silicon (a-Si) | Dry etching ($Cl_2$) |
| Support layer (605) | Silicon oxide (SiOx) | BOE wet etching |
| Sacrificial layer (607) | Amorphous silicon (a-Si) | Dry etching ($Cl_2$) |
| Top gate layer (610) | Silicon oxide (SiOx) | BOE wet etching |
| Thin film (612) | Titanium oxide (TiOx) | Dry etching ($Cl_2$) or wet etching (Hydrogen Peroxide) |
| Final etch | Etching amorphous silicon (a-Si) | Gas etching ($XeF_2$) |

TABLE 4

Choice 3

| Name | Material | Etch Mode |
|---|---|---|
| Lifter layer (603) | Molybdenum (Mo) | PAN wet etching or dry etching ($Cl_2/SF_6$) |
| Support layer (605) | Amorphous silicon (a-Si) | Dry etching ($Cl_2$) |
| Sacrificial layer (607) | Silicon oxide (SiOx) | BOE wet etching |
| Top gate layer (610) | Amorphous silicon (a-Si) | Dry etching ($Cl_2$) |
| Thin film (612) | Titanium oxide (TiOx) | Dry etching ($Cl_2$) or wet etching (Hydrogen Peroxide) |
| Final etch | Etching silicon oxide (SiOx) and molybdenum (Mo) | BOE wet etching and PAN wet etching |

TABLE 5

Choice 4

| Name | Material | Etch Mode |
|---|---|---|
| Lifter layer (603) | Molybdenum (Mo) | Dry etching ($SF_6$) |
| Support layer (605) | Aluminum alloy (Al Alloy) | Wet etching ($H_3PO_4$) |
| Sacrificial layer (607) | Molybdenum (Mo) | Dry etching ($SF_6$) |
| Top gate layer (610) | Aluminum alloy (Al Alloy) | Wet etching ($H_3PO_4$) |
| Thin film (612) | Titanium oxide (TiOx) | Dry etching ($Cl_2$) or wet etching (Hydrogen Peroxide) |
| Final etch | Etching Molybdenum (Mo) | Gas etching ($XeF_2$) |

TABLE 6

Choice 5

| Name | Material | Etch Mode |
|---|---|---|
| Lifter layer (603) | Silicon nitride (SiNx) | Wet etching (dilute HF) |
| Support layer (605) | Molybdenum (Mo) | PAN wet etching |
| Sacrificial layer (607) | Silicon nitride (SiNx) | Wet etching (dilute HF) |
| Top gate layer (610) | Molybdenum (Mo) | PAN wet etching |
| Thin film (612) | Titanium oxide (TiOx) | Dry etching ($Cl_2$) or wet etching (Hydrogen Peroxide) |
| Final etch | Etching silicon nitride (SiNx) | Wet etching (dilute HF) |

TABLE 7

Choice 6

| Name | Material | Etch Mode |
|---|---|---|
| Lifter layer (603) | Molybdenum (Mo) | PAN wet etching |
| Support layer (605) | Silicon nitride (SiNx) | Wet etching (dilute HF) |
| Sacrificial layer (607) | Molybdenum (Mo) | PAN wet etching |
| Top gate layer (610) | Silicon nitride (SiNx) | Wet etching (dilute HF) |
| Thin film (612) | Titanium oxide (TiOx) | Dry etching ($Cl_2$) or wet etching (Hydrogen Peroxide) |
| Final etch | Etching Molybdenum (Mo) | PAN wet etching |

With reference to FIGS. 13 to 24 for cross-sectional views of a manufacturing flow of a nano filter structure in accordance with a second preferred embodiment of the present invention, FIGS. 13A to 24A are cross-sectional views of a manufacturing process of a bottom gate as indicated by a cross-section line AA' of FIG. 5, and FIGS. 13B to 24B are cross-sectional views of a manufacturing process of a bottom gate as indicated by a cross-section line BB' of FIG. 5, and FIGS. 13C to 24C are cross-sectional views of a manufacturing process of a bottom gate as indicated by a cross-section line CC' of FIG. 5. The second preferred embodiment is similar to the first preferred embodiment having a layered structure, and using an etching mode to produce each filter channel. However, the layered structure of the second preferred embodiment is provided by a one-time formation method, and each step of the manufacturing procedure is illustrated by FIGS. 13 to 24.

Figure 13A:
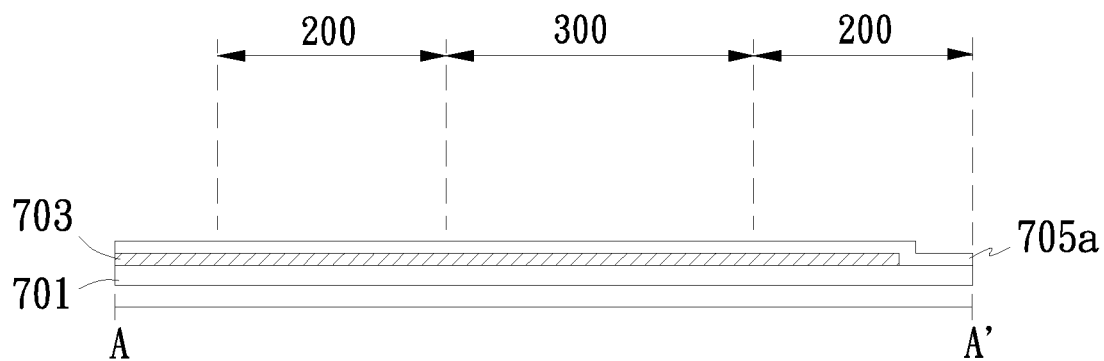
FIGS. 13 A-C, 14 A-C, 15 A-C, 16 A-C, 17 A-C, 18 A-C, 19 A-C, 20 A-C, 21 A-C, 22 A-C, 23 A-C, and 24 A-C are cross-sectional views of a manufacturing process of a nano filter structure in accordance with a second preferred embodiment of the present invention.
Figure 13B:
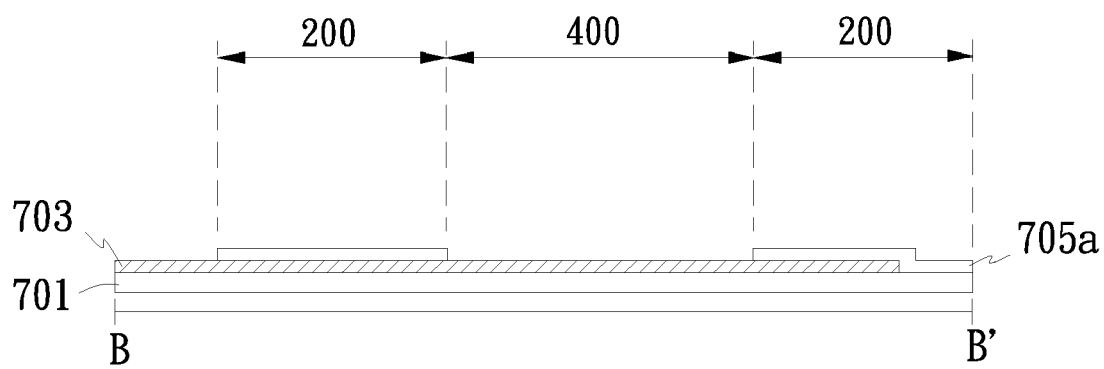
Figure 13C:
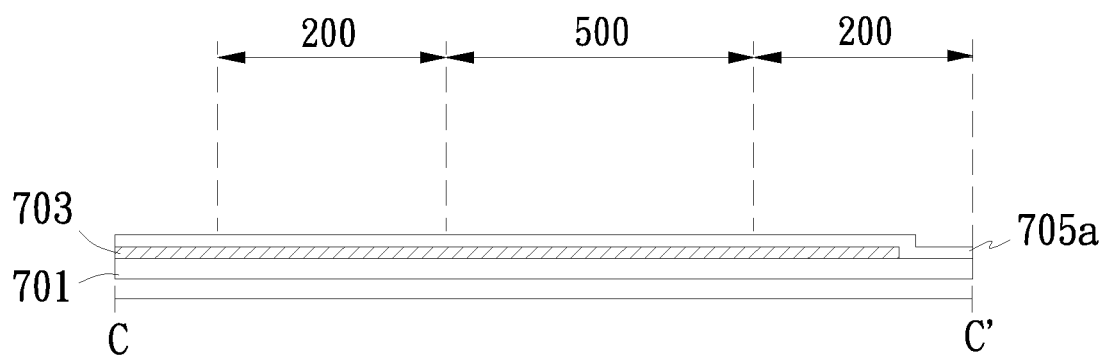

In the second preferred embodiment as shown in FIGS. 13A, 13B and 13C, the nano filter structure comprises a support region 200, a top opening region 300, a bottom opening region 400 and a sidewall gate region 500. In Step (B1), a substrate 701 such as a glass substrate, a wafer substrate, a plastic substrate or any other equivalent substrate is provided, and a patterned lifter layer 703 is formed on the substrate 701. In Step (B2), a patterned first support layer 705a is formed at a portion of the lifter layer 703 and a portion of the substrate 701, such that the first support layer 705a is disposed on the lifter layer 703 of the support region 200, top opening region 300 and sidewall gate region 500, but the bottom opening region 400 does not include the first support layer 705a.

Figure 14A:
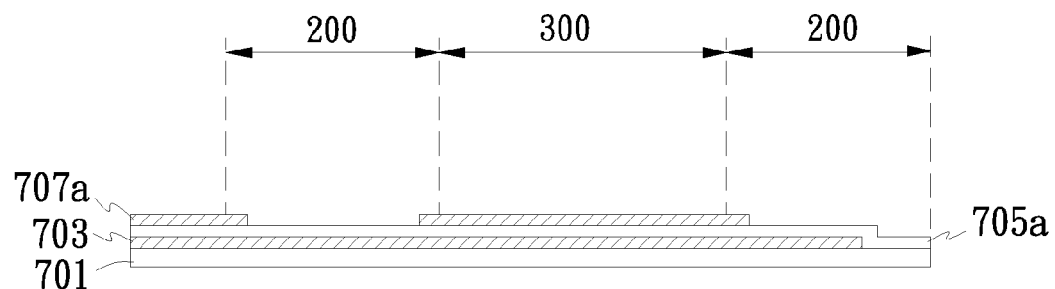
Figure 14B:
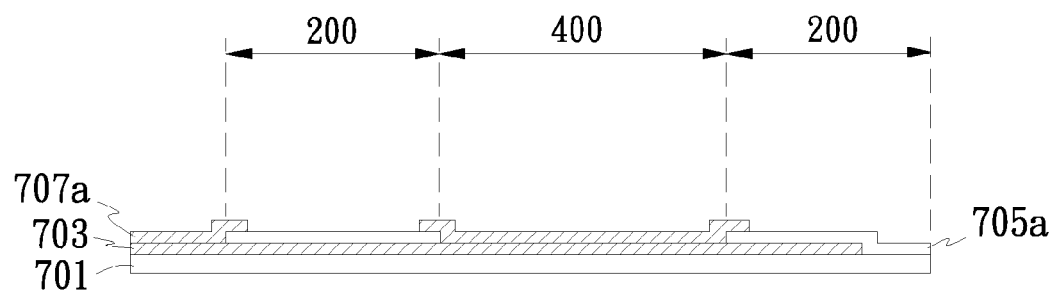
Figure 14C:
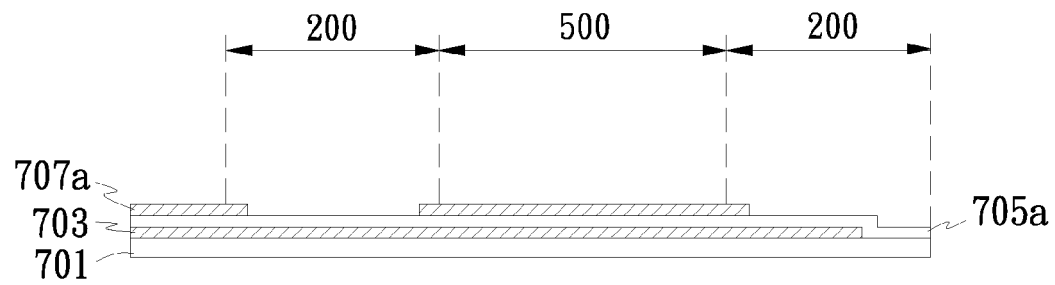

With reference to FIGS. 14A, 14B and 14C, Step (B3) is carried out, wherein sputtering, chemical vapor deposition, physical vapor deposition or any other equivalent method, as well as lithography and etching technologies are used for forming a first sacrificial layer 707a separately on the lifter layer 703 of the bottom opening region 400, and on the first support layer 705a of the top opening region 300 and the sidewall gate region 500, and the sacrificial layer has a thickness (or height) smaller than or equal to 300 nm.

Figure 15A:
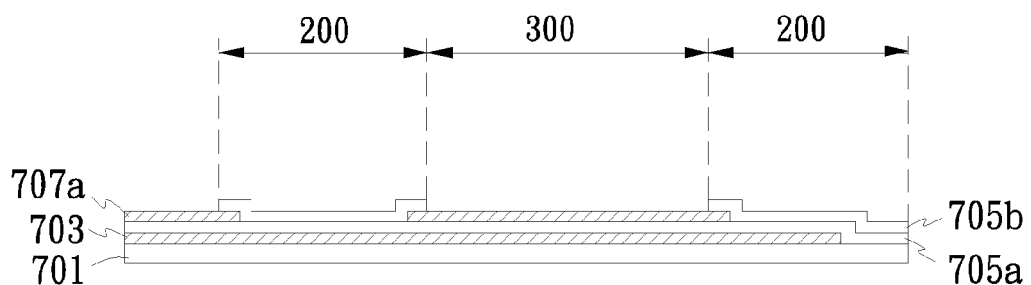
Figure 15B:
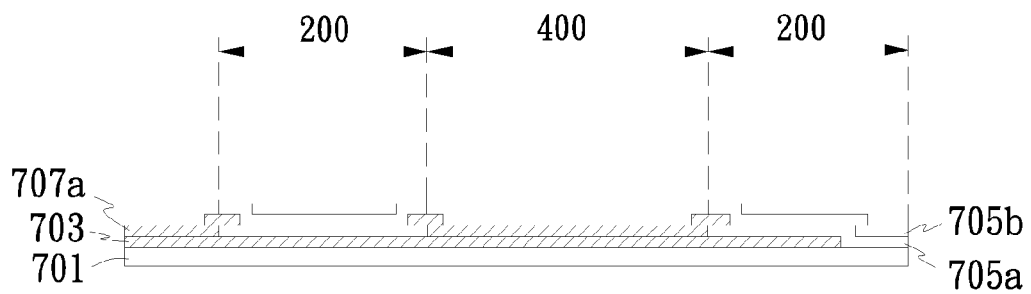
Figure 15C:
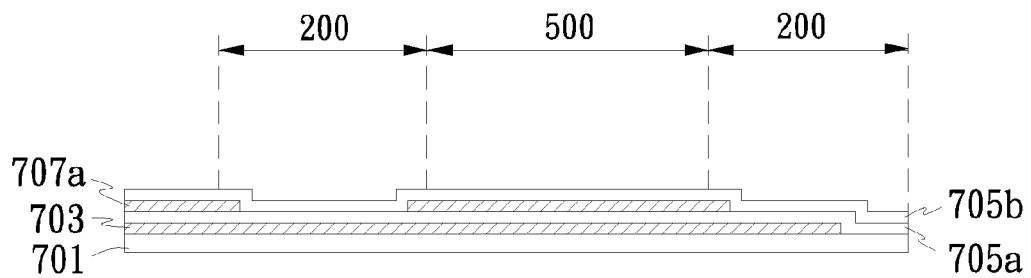

With reference to FIGS. 15A, 15B and 15C for Step (B4), sputtering, chemical vapor deposition, physical vapor deposition or any other equivalent method as well as lithography and etching technologies are used for forming a second support layer 705b separately on the first sacrificial layer 707a of the sidewall gate region 500, and on the first support layer 705a of the support region 200. In FIG. 15C, the second support layers 705b of the support region 200 and sidewall gate region 500 are continuous layered structures, and a filterable grating 142 is formed at the support layer of the sidewall gate region 500 as shown in FIGS. 2 to 4. In FIGS. 15A, 15B and 15C, a bottom gate 120 is formed on the first support layer 705a of the support region 200, the top opening region 300 and the sidewall gate region 500 shown in FIGS. 2 to 4.

Figure 16A:
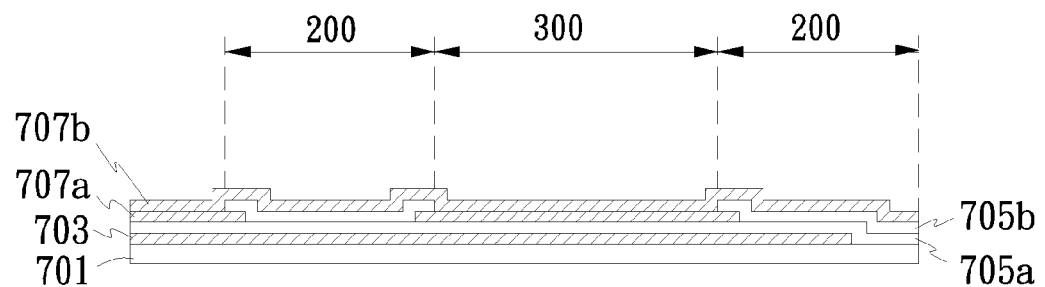
Figure 16B:
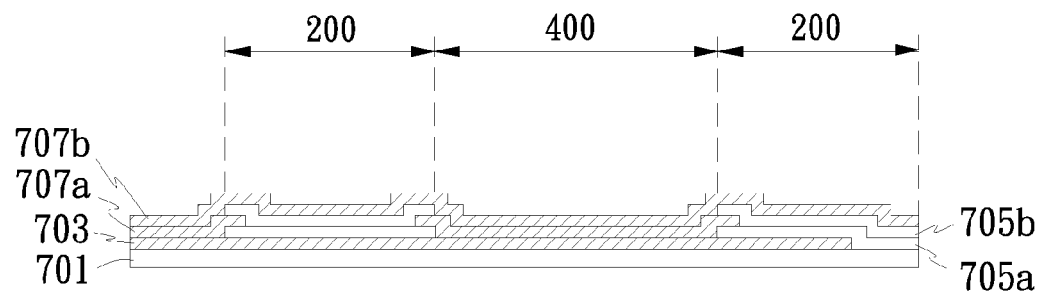
Figure 16C:
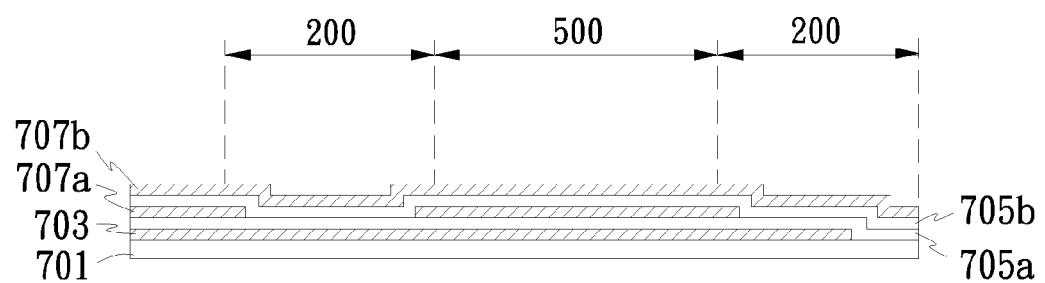

With reference to FIGS. 16A, 16B and 16C for Step (B5), sputtering, chemical vapor deposition, physical vapor deposition or any other equivalent method is used for forming a second sacrificial layer 707b separately on the top opening region 300, the bottom opening region 400, the sidewall gate regions 500 and the support regions 200.

Figure 17A:
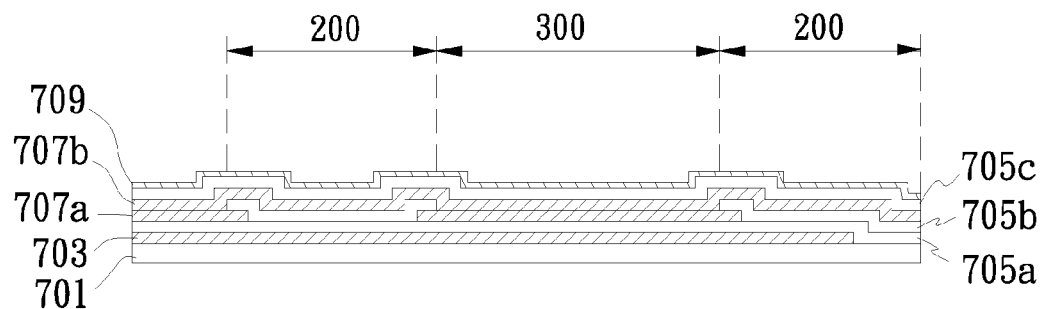
Figure 17B:
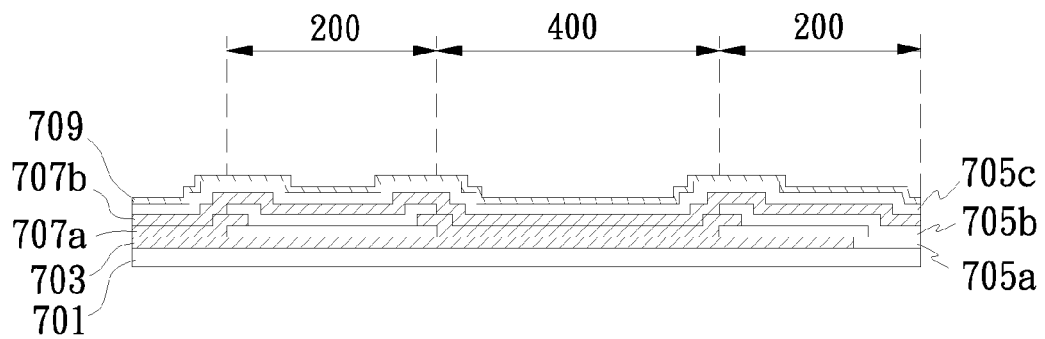
Figure 17C:
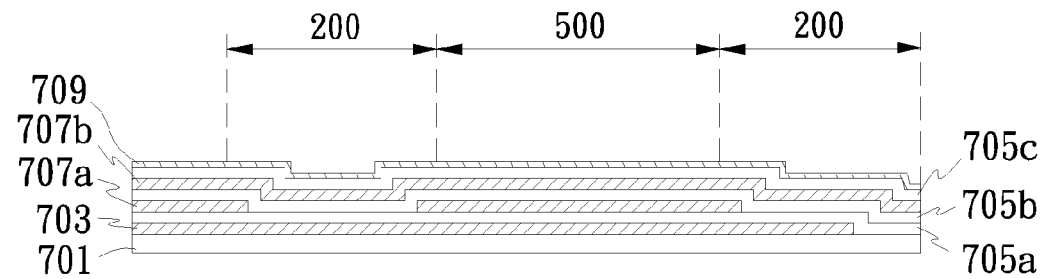

With reference to FIGS. 17A, 17B and 17C for Step (B6), sputtering, chemical vapor deposition, physical vapor deposition or any other equivalent method is used for forming a third support layer 705c separately on the top opening region 300, the bottom opening region 400, the sidewall gate regions 500 and the support regions 200. Step (B7) is carried out, wherein sputtering, chemical vapor deposition, physical vapor deposition or any other equivalent method is used for forming a protective layer 709 separately on the top opening region 300, the bottom opening region 400, the sidewall gate region 500 and the support region 200.

Figure 18A:
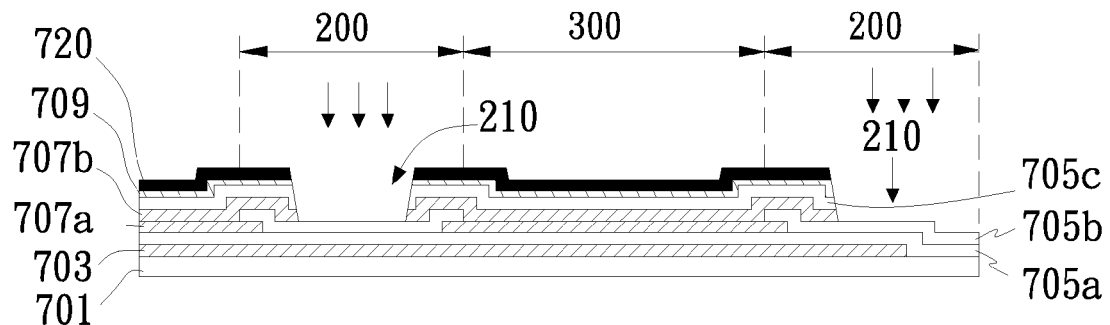
Figure 18B:
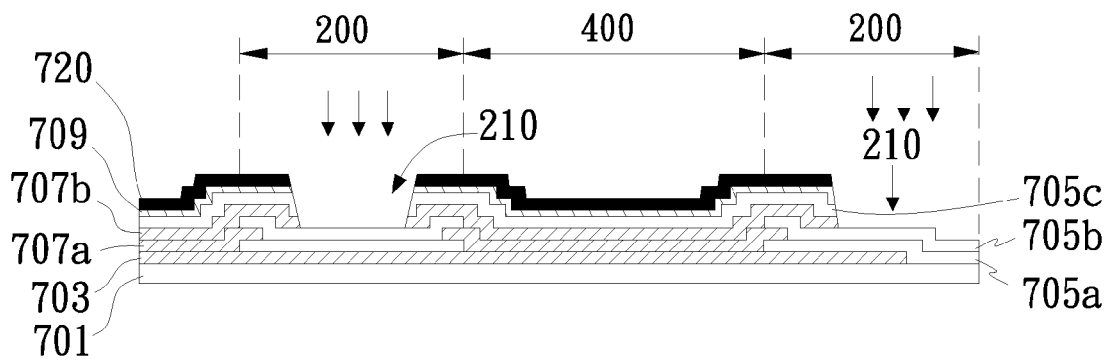
Figure 18C:
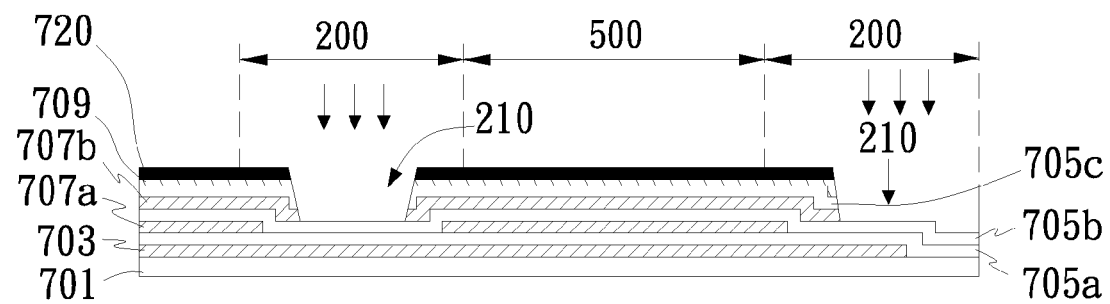

With reference to FIGS. 18A, 18B and 18C for Step (B8), the support regions 200 and removing at least the third support layer 705c are etched to facilitate forming a support groove 210 in each support region 200. Since an anisotropic etching process of a higher power is required for forming the support grooves 210, a photoresist at an open edge of the patterned photoresist layer 720 may be removed by the high power anisotropic etching process easily, and the film layer under the photoresist layer 720 can be etched easily, so that a uniform line width cannot be controlled easily. Particularly for a large number of filter channels, the high power anisotropic etching effect takes a longer time, and the edge of an opening of the photoresist layer 720 will be removed more severely. With the protective layer 709, the film layer under the protective layer can be protected from the high power anisotropic etching effect, and the material of the protective layer 709 can resist the high power etching For example, the high power anisotropic etching can be a dry etching technology, and the protective layer 709 has a higher level of reaction with wet etching, and thus the wet etching is performed to etch and create an opening from protective layer 709 first, and then the high power dry etching is performed to form the support grooves 210. With the photoresist layer 720 and the protective layer 709, the film layer can be protected from being damaged.

In Step (B8), at least the third support layer 705c is removed, and an etching end point detector (EPD) is used for controlling the etching depth. Persons ordinarily skilled in the art should understand that any other equivalent etching control can be used for the present invention.

Figure 19A:
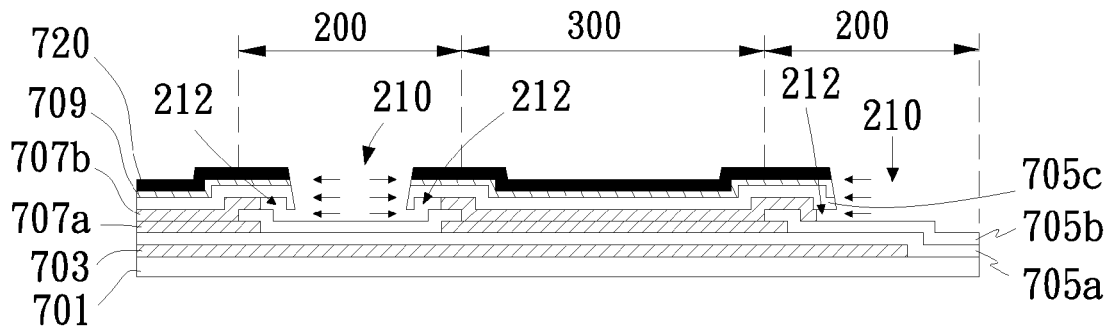
Figure 19B:
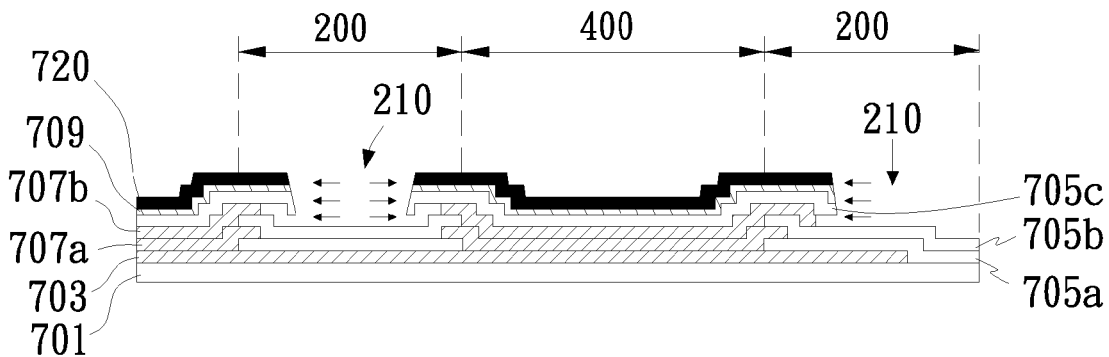
Figure 19C:
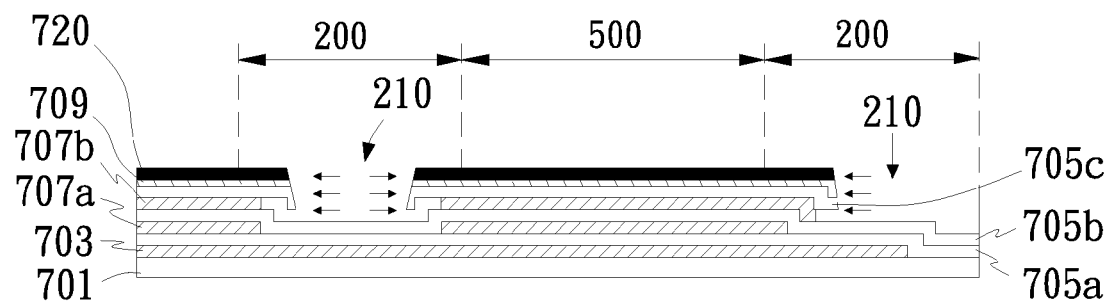

With reference to FIGS. 19A, 19B and 19C, in Step (B9), a side etching is performed in the support grooves 210 and a portion of the sacrificial layer is removed to form a plurality of support side-wing grooves 212 in the support regions 200 and the photoresist layer 720 is removed after the support side-wing grooves 212 are formed.

Figure 20A:
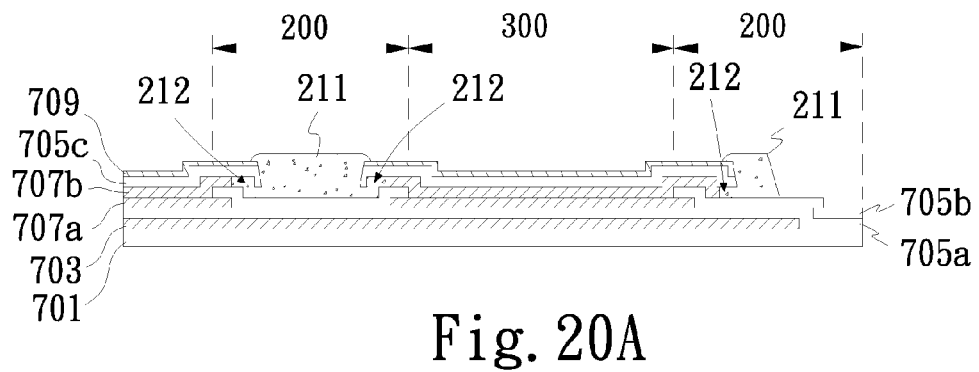
Figure 20B:
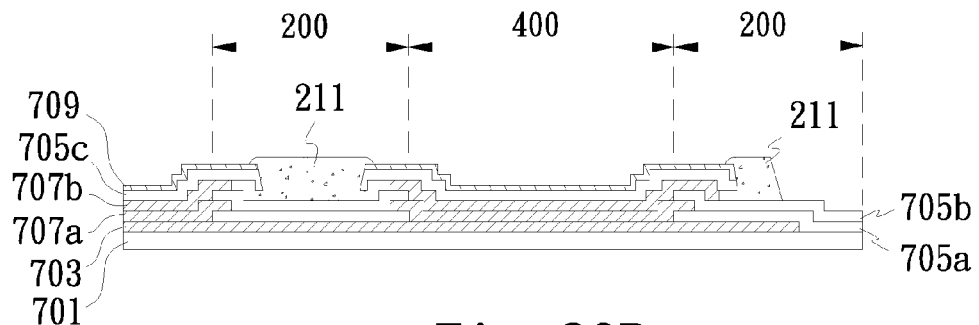
Figure 20C:
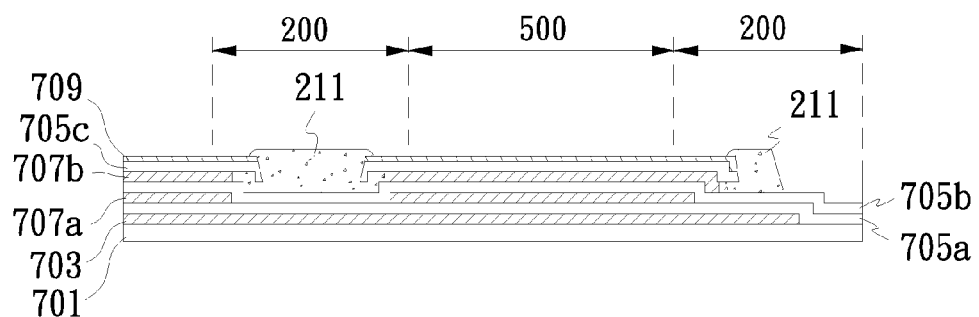

With reference to FIGS. 20A, 20B and 20C for Step (B10), the support grooves 210 and the support side-wing grooves 212 are filled to form a plurality of fillers 211. In the figures, the fillers 211 are main supports in the support regions 200, and an extension of the side-wing groove 212 provides a more secured overall structure. The fillers 211 are made of a flexible material such as polymer to provide a more flexibility to the filter structure. The polymer is filled into the support grooves 210 and the support side-wing grooves 212 first, and then heated by an oven to solidify the polymer.

Figure 21A:
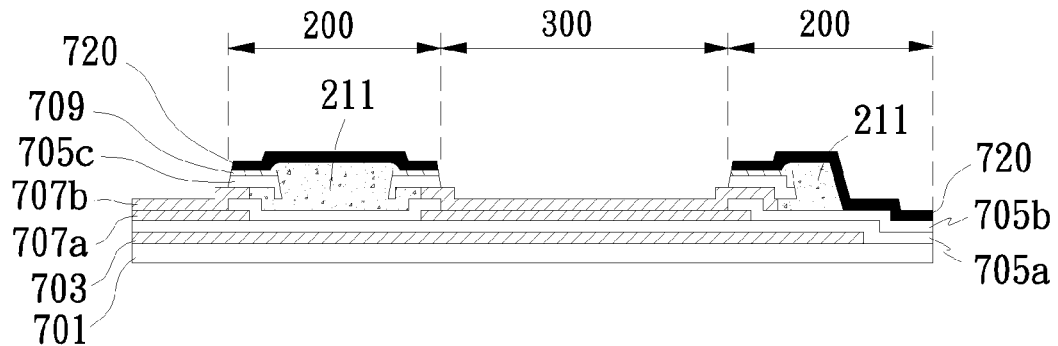
Figure 21B:
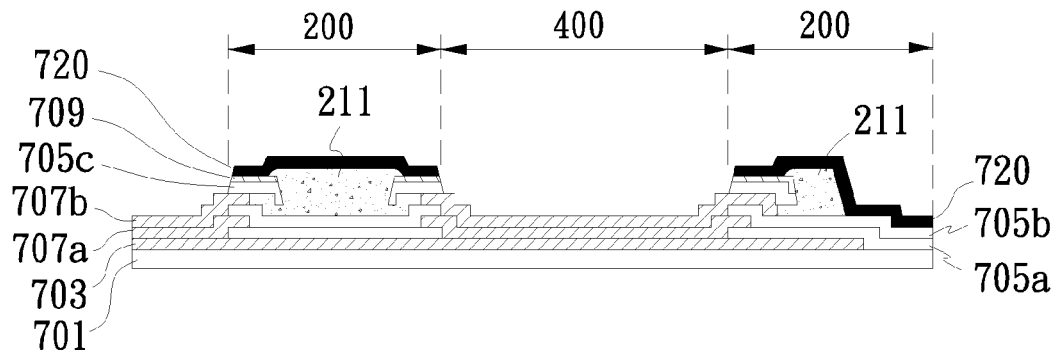
Figure 21C:
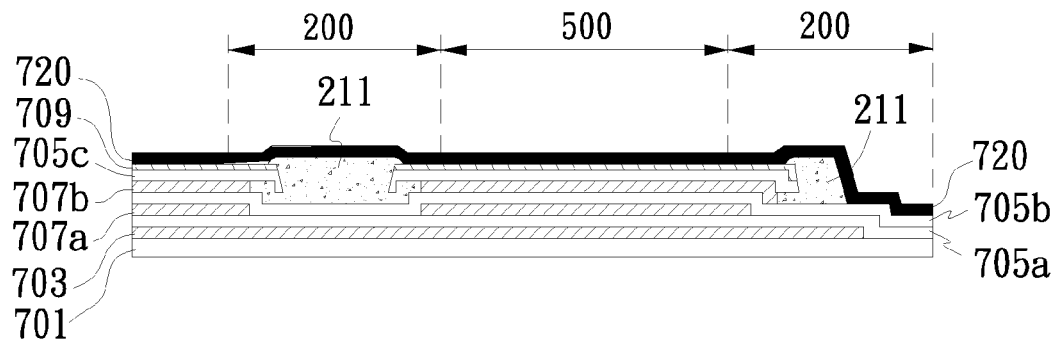

With reference to FIGS. 21A, 21B and 21C for Step (B11), the top opening region 300 and the bottom opening region 400 are etched, and at least the third support layer 705c is removed. Similar to Step (B8), a photoresist layer 720 is used together with different etching technologies to etch an opening from the protective layer, and then a high power anisotropic etching is performed. Similarly, the etching depth is controlled such that at least the third support layer 705c is removed. Alternatively, the aforementioned etching end point detector can be used for achieving the effect of removing the photoresist layer 720 after the etching is completed.

Figure 22A:
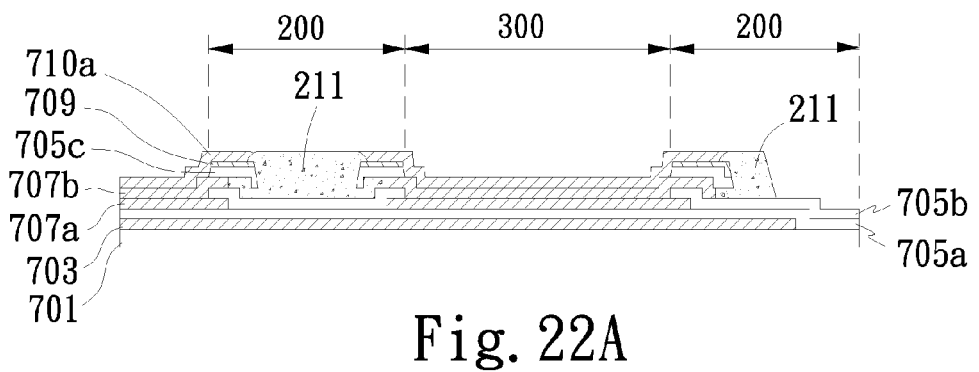
Figure 22B:
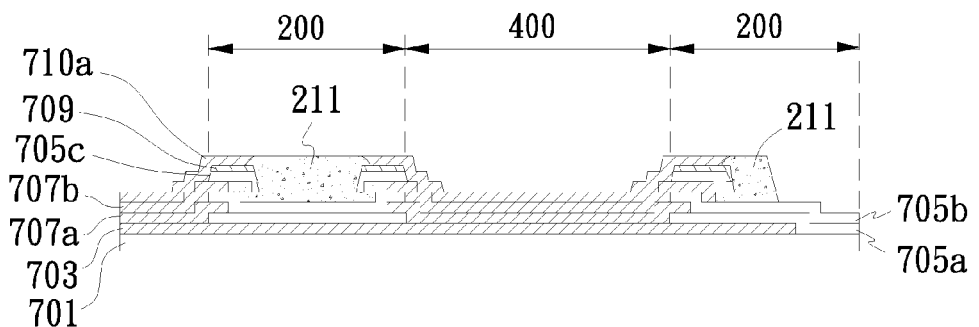
Figure 22C:
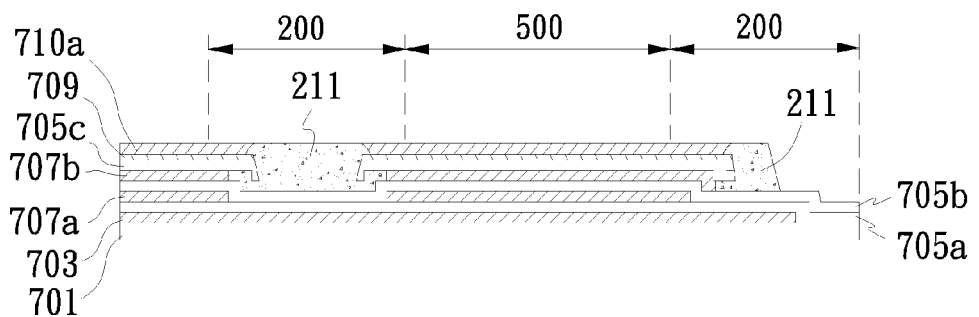

With reference to FIGS. 22A, 22B and 22C for Step (B12), sputtering, chemical vapor deposition, physical vapor deposition or any other equivalent method as well as lithography and etching technologies are used to carry out this step, wherein a patterned first channel sacrificial layer 710a is formed separately on the top opening region 300, the bottom opening region 400, the sidewall gate regions 500 and a portion of the support regions 200.

Figure 23A:
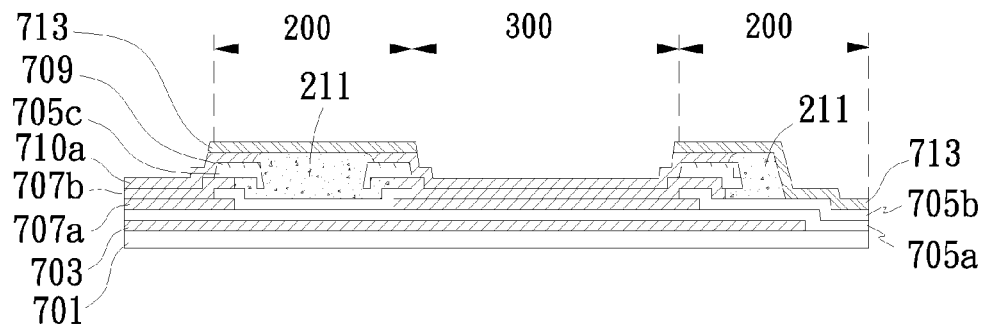
Figure 23B:
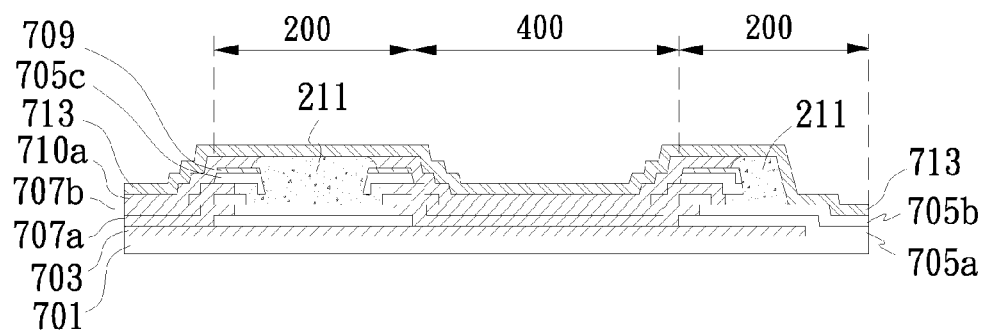
Figure 23C:
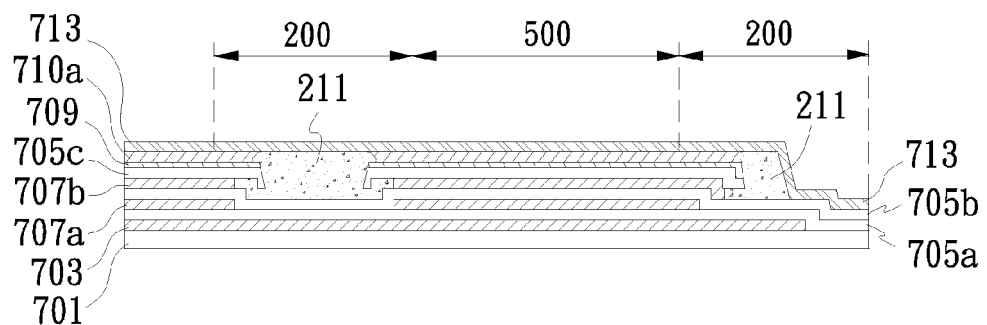

With reference to FIGS. 23A, 23B and 23C for Step (B13), sputtering, chemical vapor deposition, physical vapor deposition or any other equivalent method as well as lithography and etching technologies are used to carry out this step, wherein a top gate layer 713 is formed separately on the bottom opening region 400, the sidewall gate regions 500 and the support regions 200. In FIG. 23B, a top gate 110 is formed on the top gate layer 713 of the bottom opening region 400 as shown in FIGS. 2 to 4.

Figure 24A:
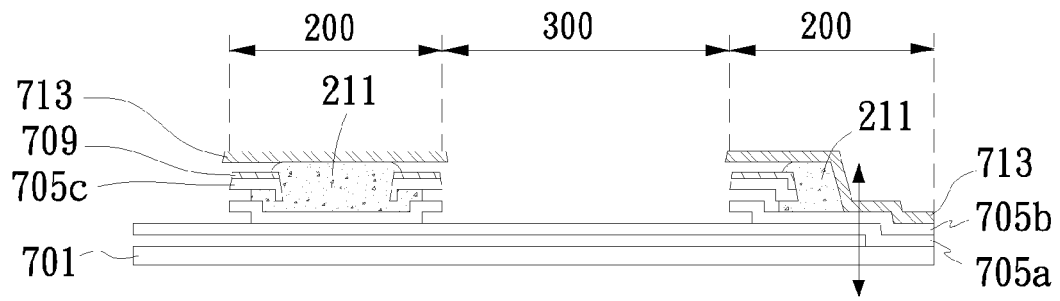
Figure 24B:
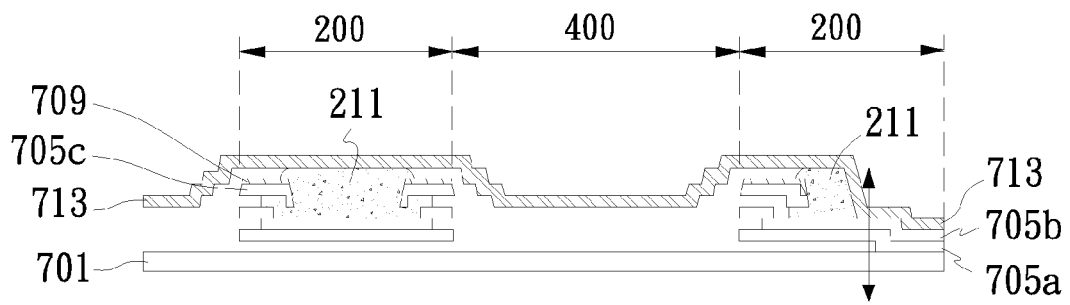
Figure 24C:
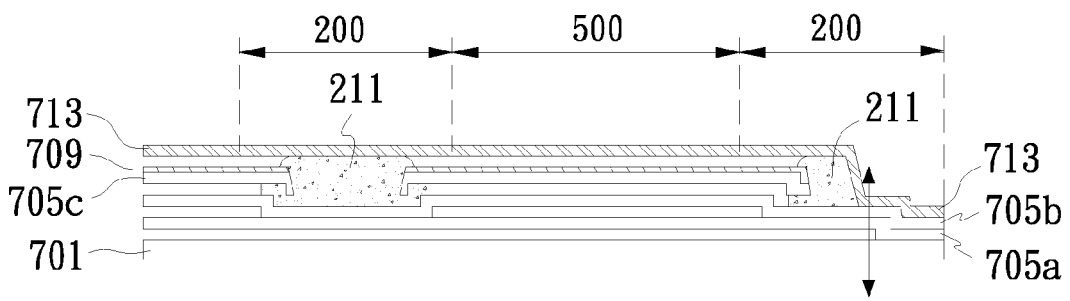

With reference to FIGS. 24A, 24B and 24C for Step (B14), the final etch is carried out, and an etching technology such as dry etching, wet etching, gas etching or any other equivalent method is used to remove the lifter layer 703 and all sacrificial layers 707a, 707b, 710a. Finally, Step (B15) is carried out to remove the substrate 701 to form a nano filter structure as shown in FIG. 3 or 4. The substrate 701 can be obtained by a scribe or any other equivalent technology.

Figure 25A:
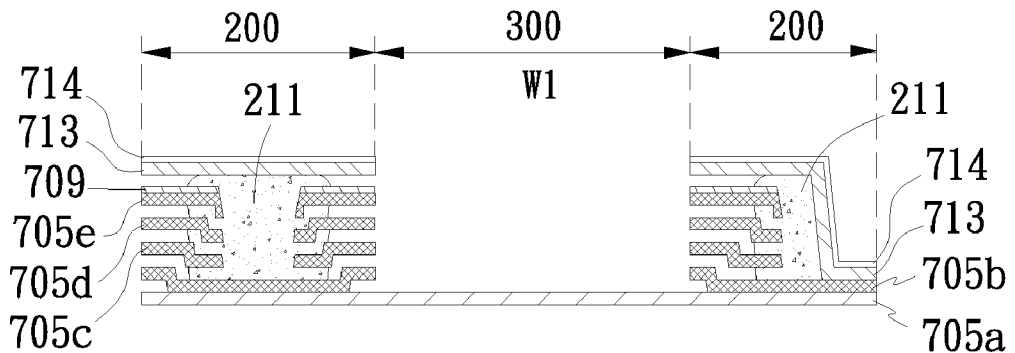
FIGS. 25 A to 25 C are a cross-sectional view of a portion of a nano filter structure having five filter channels.
Figure 25B:
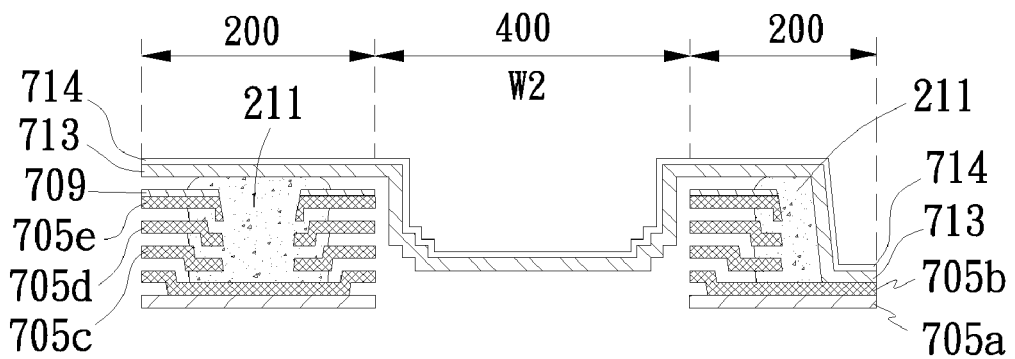
Figure 25C:
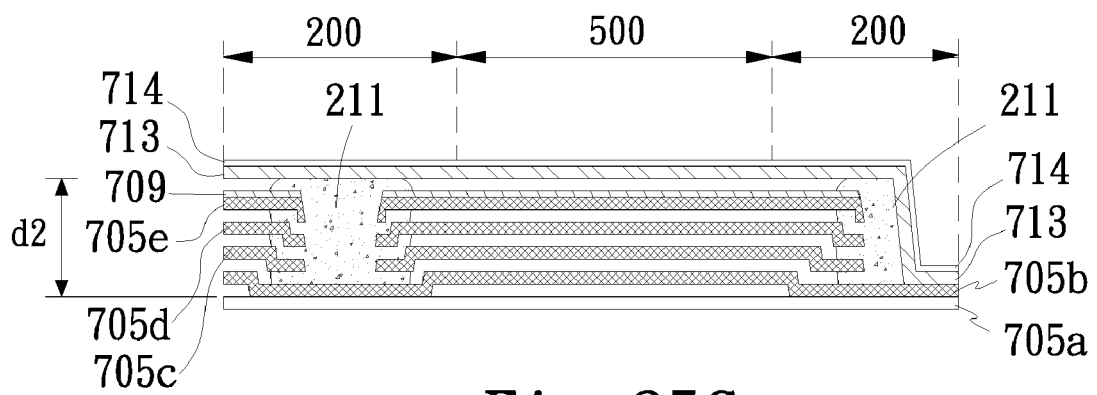

With reference to FIGS. 25A, 25B and 25C for cross-sectional views of a nano filter structure having five filter channels, w1, w2 and d2 correspond to w1, w2 and d2 as shown in FIGS. 1 and 2, wherein the first to fifth support layers corresponding to 705a to 705e respectively. In FIGS. 13 to 24, the manufacturing method of a nano filter structure having three filter channels is described, but more filter channels can increase the aperture ratio. Based on the foregoing method, Step (B6-1) is carried out after Step (B6) has taken place. In other words, Steps (B5) and (B6) of the manufacturing process are repeated in sequency to increase the quantity of filter channels, or the support layers and the sacrificial layers are stacked alternately to form more filter channels. In Step (B6-1), the last step can be Step (B5), such that the last layer so formed is a sacrificial layer, and the protective layer 709 can be used as a support layer, and an additional filter channel is remained.

Figure 26A:
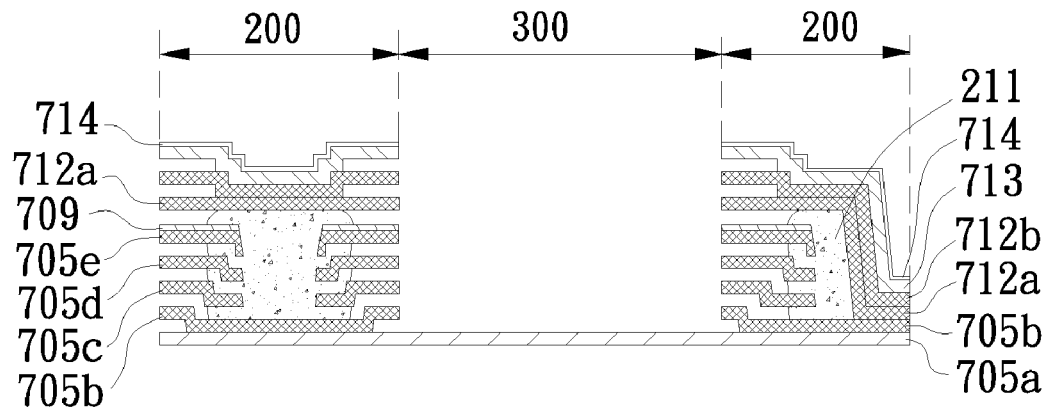
FIGS. 26 A to 26 C are a schematic view of a bottom opening region with widened channels on sides of the region in accordance with a second preferred embodiment of the present invention.
Figure 26B:
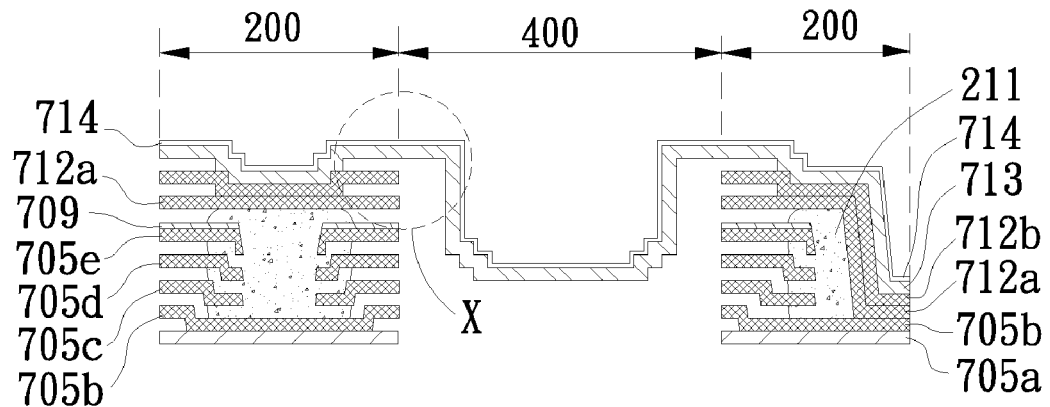
Figure 26C:
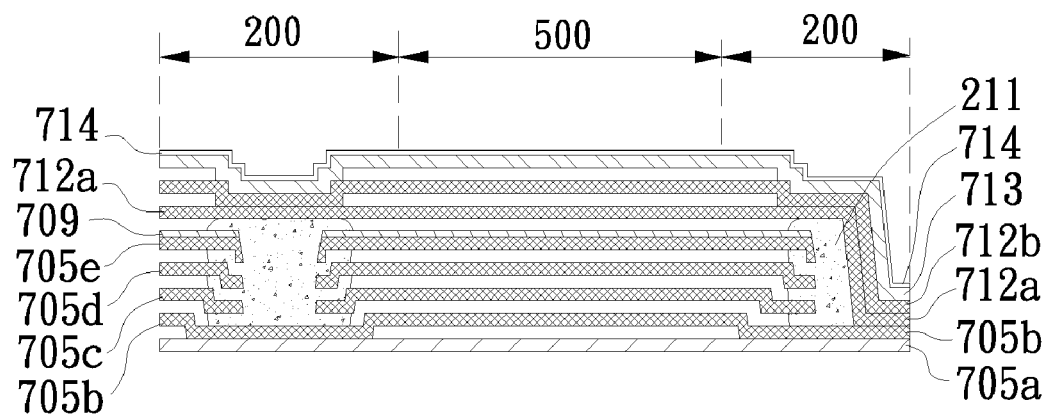

With reference to FIGS. 26A, 26B and 26C, the second preferred embodiment further includes the following two steps after Step (B12) takes place. In Step (B12-1), a patterned first channel support layer 712a is formed on the sidewall gate regions 500 and the support regions 200. In Step (B12-2), Steps (B12) and (B12-1) are repeated in sequency to form a plurality of channel support layers 712a~712b and a plurality of channel sacrificial layers, wherein the finally formed layers are channel sacrificial layers. In the aforementioned two steps, the width of the channels on sides of the bottom opening region 400 is increased (as shown in FIG. 26B). The more the quantity of formed filter channels as described in Step (B6-1), the wider are the channels on the sides of the bottom opening region 400 and the better is the effect. For example, three to four channel sacrificial layers are used for increasing the width of the channels on the sides of the bottom opening region 400. In FIGS. 26A, 26B and 26C, three channel sacrificial layers (indicated by the portion X in FIG. 26B) are used.

The number stacked layers as described in Steps (B6-1), (B12-1) and (B12-2) can be controlled or adjusted according to the actual requirement.

In the second preferred embodiment, the manufacturing method further comprises a Step (B13-1) of forming a thin film 714 on the top gate layer 713 for decomposing an organic matter (as shown in FIG. 25 or 26) after Step (B13) takes place or before the lifter layer 703 and all sacrificial layers 707a, 707b, 710a are removed. The thin film 714 can be made of a material such as titanium (Ti), titanium dioxide (TiO$_2$) or platinum (Pt) for resisting or killing viruses and bacteria, and this material is a catalyst provided for decomposing an organic matter on the filter structure. The thin film 714 can be formed by physical vapor deposition, chemical vapor deposition, sputtering or any other equivalent manufacturing process.

Tables 8 to 13 list the material, the etch mode for forming each film layer and the final etch (which is the etch mode for removing the lifter layer and all sacrificial layers) in accordance with a second preferred embodiment. Persons skilled in the art should know that the materials and etch mode are not limited to such arrangements only, but any other material and etch mode can be used for manufacturing the nano filter structure of the invention, wherein the PAN wet etching includes the composition of (Phosphorus acid+Acetic acid+Nitric acid)aq, and the BOE wet etching includes the composition of (HF+NH$_4$F)aq.

TABLE 8

| | Choice 1 | |
|---|---|---|
| Item | Material | Etch Mode |
| Lifter layer (703) | Molybdenum (Mo) | PAN wet etching or dry etching (Cl$_2$/SF$_6$) |
| Support layer (705, 712) | Silicon oxide (SiOx) | BOE wet etching |
| Sacrificial layer (707, 710) | molybdenum (Mo) | PAN wet etching or dry etching (Cl$_2$/SF$_6$) |
| Protective layer (709) | Copper (Cu) | Adopting nitric acid solution (HNO$_3$) or ammonium persulfates (APS) for wet etching |
| Support groove (210) etch mode | Etching molybdenum (Mo) and silicon oxide (SiOx) | High power dry etching (SF$_6$) |
| Support groove sidewing (212) etch mode | Etching molybdenum (Mo) | PAN wet etching |
| Sidewall gate region (500) etch mode | Etching molybdenum (Mo) and silicon oxide (SiOx) | High power dry etching (SF$_6$) |
| Top gate layer (713) | silicon oxide (SiOx) | BOE wet etching |
| Thin film (714) | Titanium oxide (TiOx) | Dry etching (Cl$_2$) or wet etching (Hydrogen Peroxide) |
| Final etch | Etching molybdenum (Mo) | PAN wet etching or gas etching (XeF$_2$) |

TABLE 9

| | Choice 2 | |
|---|---|---|
| Item | material | Etch Mode |
| Lifter layer (703) | amorphous silicon (a-Si) | Dry etching (Cl$_2$) |
| Support layer (705, 712) | silicon oxide (SiOx) | BOE wet etching |
| Sacrificial layer (707, 710) | amorphous silicon (a-Si) | Dry etching (Cl$_2$) |
| Protective layer (709) | Copper (Cu) | Adopting nitric acid solution (HNO$_3$) or ammonium persulfates (APS) for wet etching |
| Support groove (210) etch mode | Etching amorphous silicon (a-Si) and silicon oxide (SiOx) | High-power dry etching (Cl$_2$ + SF$_6$) |
| Support groove sidewing (212) etch mode | Etching amorphous silicon (a-Si) | Cl$_2$ rich low-power dry etching or gas etching (XeF$_2$) |
| Sidewall gate region (500) etch mode | Etching amorphous silicon (a-Si) and silicon oxide (SiOx) | High-power dry etching (Cl$_2$ + SF$_6$) |
| Top gate layer (713) | Silicon oxide (SiOx) | BOE wet etching |
| Thin film (714) | Titanium oxide (TiOx) | Dry etching (Cl$_2$) or wet etching (Hydrogen Peroxide) |
| Final etch | Etching amorphous silicon (a-Si) | Gas etching (XeF$_2$) |

TABLE 10

| | Choice 3 | |
|---|---|---|
| Item | Material | Etch Mode |
| Lifter layer (703) | Molybdenum (Mo) | PAN wet etching or dry etching (Cl$_2$/SF$_6$) |
| Support layer (705, 712) | Amorphous silicon (a-Si) | Dry etching (Cl$_2$) |
| Sacrificial layer (707, 710) | Silicon oxide (SiOx) | BOE wet etching |
| Protective layer (709) | Copper (Cu) | Adopting nitric acid solution (HNO$_3$) or ammonium persulfates (APS) for wet etching |
| Support groove (210) etch mode | Etching silicon oxide (SiOx) and amorphous silicon (a-Si) | High-power dry etching (Cl$_2$ + SF$_6$) |
| Support groove sidewing (212) etch mode | Etching silicon oxide (SiOx) | BOE wet etching |
| Sidewall gate region (500) etch mode | Etching silicon oxide (SiOx) and amorphous silicon (a-Si) | High power dry etching (Cl$_2$ + SF$_6$) |
| Top gate layer (713) | Amorphous silicon (a-Si) | Dry etching (Cl$_2$) |
| Thin film (714) | Titanium oxide (TiOx) | Dry etching (Cl$_2$) or wet etching (Hydrogen Peroxide) |
| Final etch | Etching silicon oxide (SiOx) and molybdenum (Mo) | BOE wet etching first, and then PAN wet etching |

TABLE 11

| | Choice 4 | |
|---|---|---|
| Item | Material | Etch Mode |
| Lifter layer (703) | Molybdenum (Mo) | Dry etching (SF$_6$) |
| Support layer (705, 712) | Aluminum Alloy (Al Alloy) | Wet etching (H$_3$PO$_4$) |
| Sacrificial layer (707, 710) | Molybdenum (Mo) | Dry etching (SF$_6$) |

TABLE 11-continued

Choice 4

| Item | Material | Etch Mode |
|---|---|---|
| Protective layer (709) | Copper (Cu) | Adopting nitric acid solution (HNO$_3$) or ammonium persulfates (APS) for wet etching |
| Support groove (210) etch mode | Etching molybdenum (Mo) and aluminum alloy | high power dry etching (Cl$_2$ + SF$_6$) |
| Support groove sidewing (212) etch mode | Etching molybdenum (Mo) | Gas etching (XeF$_2$) |
| Sidewall gate region (500) etch mode | Etching molybdenum (Mo) and aluminum alloy | High power dry etching (Cl$_2$ + SF$_6$) |
| Top gate layer (713) | Aluminum alloy (Al Alloy) | Wet etching (H$_3$PO$_4$) |
| Thin film (714) | titanium oxide (TiOx) | Dry etching (Cl$_2$) or wet etching (Hydrogen Peroxide) |
| Final etch | Etching molybdenum (Mo) | gas etching (XeF$_2$) |

TABLE 12

Choice 5

| Item | material | Etch Mode |
|---|---|---|
| Lifter layer (703) | Silicon nitride (SiNx) | Wet etching (dilute HF) |
| Support layer (705, 712) | Molybdenum (Mo) | PAN wet etching |
| Sacrificial layer (707, 710) | Silicon nitride (SiNx) | Wet etching (dilute HF) |
| Protective layer (709) | Copper (Cu) | Adopting nitric acid solution (HNO$_3$) or ammonium persulfates (APS) for wet etching |
| Support groove (210) etch mode | Etching silicon nitride (SiNx) and molybdenum (Mo) | High power dry etching (CF$_4$ + SF$_6$) |
| Support groove sidewing (212) etch mode | Etching silicon nitride (SiNx) | Wet etching (dilute HF) |
| Sidewall gate region (500) etch mode | Etching silicon nitride (SiNx) and molybdenum (Mo) | High power dry etching (CF$_4$ + SF$_6$) |
| Top gate layer (713) | Molybdenum (Mo) | PAN wet etching |
| Thin film (714) | Titanium oxide (TiOx) | Dry etching (Cl$_2$) or wet etching (Hydrogen Peroxide) |
| Final etch | Etching silicon nitride (SiNx) | Wet etching (dilute HF) |

TABLE 13

Choice 6

| Item | Material | Etch Mode |
|---|---|---|
| Lifter layer (703) | Molybdenum (Mo) | PAN wet etching |
| Support layer (705, 712) | Silicon nitride (SiNx) | Wet etching (dilute HF) |
| Sacrificial layer (707, 710) | Molybdenum (Mo) | PAN wet etching |
| Protective layer (709) | Copper (Cu) | Adopting nitric acid solution (HNO$_3$) or ammonium persulfates (APS) for wet etching |
| Support groove (210) etch mode | Etching molybdenum (Mo) and silicon nitride (SiNx) | High-power dry etching (CF$_4$ + SF$_6$) |
| Support groove sidewing (212) etch mode | Etching molybdenum (Mo) | PAN wet etching |
| Sidewall gate region (500) etch mode | Etching molybdenum (Mo) and silicon nitride (SiNx) | High-power dry etching (CF$_4$ + SF$_6$) |
| Top gate layer (713) | Silicon nitride (SiNx) | Wet etching (dilute HF) |
| Thin film (714) | Titanium oxide (TiOx) | Dry etching (Cl$_2$) or wet etching (Hydrogen Peroxide) |
| Final etch | Etching molybdenum (Mo) | PAN wet etching |

In the manufacturing methods of the aforementioned two preferred embodiments, the top gate 110 is formed in the bottom opening region 400 as shown in FIGS. 2 to 4, and the bottom gate 120 is formed in the top opening region 300 as shown in FIGS. 2 to 4, and the sidewall gate 140 is formed in the sidewall gate regions 500 as shown in FIGS. 2 to 4, and the supports 130 are formed in the support regions 200 as shown in FIGS. 2 to 4. In addition, the support regions 200 are situated at intersections of the sidewall gate regions 500.

Therefore, the nano filter structure manufactured by the semiconductor process technology can achieve a nano filterable grating easily and manufacture the nano filter structure quickly. The thickness of each film layer can be controlled effectively and adjusted according to actual needs, and the thickness of the sacrificial layer can be controlled to determine the filter grading of the filter structure. One of the top and bottom gates in micron scale can be used for preliminarily filtering a micron-scale convected airflow to extend the life of the filter material. The multilayer design of the stacked filterable grating can improve the aperture ratio of the filter material, so that users can inhale or exhale through the filter material easily. A thin film formed on a surface of the filter structure for decomposing an organic matter can be used for resisting or killing viruses and bacteria.

While the invention has been described by means of specific embodiments, numerous modifications and variations could be made thereto by those skilled in the art without departing from the scope and spirit of the invention set forth in the claims.

What is claimed is:

1. A manufacturing method of a nano filter structure for breathing, and the nano filter structure comprising a plurality of top opening regions, a plurality of bottom opening regions, a plurality of sidewall gate regions and a plurality of support regions, and each sidewall gate region being disposed adjacent to a top opening region and a bottom opening region, and the support regions being disposed at an interaction of two sidewall gate regions, and the manufacturing method comprising the steps of:
   (B1) forming a patterned lifter layer on a substrate;
   (B2) forming a patterned first support layer on a portion of the lifter layer and a portion of the substrate, such that the bottom opening regions do not include the first support layer;
   (B3) forming a patterned first sacrificial layer on the bottom opening regions, the top opening regions and the sidewall gate regions;
   (B4) forming a patterned second support layer on the sidewall gate regions and the support regions;
   (B5) forming a second sacrificial layer on the top opening regions, the bottom opening regions, the sidewall gate regions and the support regions;

(B6) forming a third support layer on the top opening regions, the bottom opening regions, the sidewall gate regions and the support regions;

(B7) forming a protective layer on the top opening regions, the bottom opening regions, the sidewall gate regions and the support regions;

(B8) etching the support regions and removing at least the third support layer to form a support groove in each support region;

(B9) performing a side etch in the support grooves, and removing a portion of the sacrificial layers to form a plurality of support side-wing grooves;

(B10) filling the support grooves and the support side-wing grooves to form a plurality of fillers;

(B11) etching the top opening regions and the bottom opening regions, and removing at least the third support layer;

(B12) forming a patterned first channel sacrificial layer in the top opening regions, the bottom opening regions, the sidewall gate regions and a portion of the support regions;

(B13) forming a top gate layer in the bottom opening regions, the sidewall gate regions and the support regions;

(B14) removing the lifter layer and all sacrificial layers; and (B15) removing the substrate;

wherein each sacrificial layer so formed has a thickness smaller than or equal to 300 nm.

2. The manufacturing method of claim 1, wherein the first support layer is patterned in Step (B2), such that the top opening regions and the bottom opening regions have sides with a micron-scale length.

3. The manufacturing method of claim 1, further comprising a step of defining the sidewall gate regions at peripheries of the top opening regions and the bottom opening regions in Step (B4).

4. The manufacturing method of claim 1, further comprising a Step (B6-1) that repeats Steps (B5) and (B6) in sequency to form a plurality of support layers and a plurality of sacrificial layers, after Step (B6) takes place.

5. The manufacturing method of claim 4, wherein the last layer formed in Step (B6-1) is a sacrificial layer.

6. The manufacturing method of claim 1, further comprising the steps of:
(B12-1) forming a patterned first channel support layer in the sidewall gate regions and the support regions; and
(B12-2) repeating Steps (B12) and (B12-1) in sequency to form a plurality of channel support layers and a plurality of channel sacrificial layers, and finally forming a channel sacrificial layer, after Step (B12) takes place.

7. The manufacturing method of claim 1, further comprises a Step (B13-1) of forming a thin film on the top gate layer for decomposing an organic matter, after Step (B13) takes place.

* * * * *